(12) United States Patent
Thakur et al.

(10) Patent No.: US 9,556,118 B2
(45) Date of Patent: Jan. 31, 2017

(54) ALLOSTERIC MODULATORS OF CB1 CANNABINOID RECEPTORS

(71) Applicant: Northeastern University, Boston, MA (US)

(72) Inventors: Ganeshsingh A. Thakur, Cambridge, MA (US); Pushkar M. Kulkarni, Boston, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 14/323,492

(22) Filed: Jul. 3, 2014

(65) Prior Publication Data
US 2015/0005346 A1    Jan. 1, 2015

Related U.S. Application Data

(63) Continuation of application No. PCT/US2013/020543, filed on Jan. 7, 2013.

(60) Provisional application No. 61/583,380, filed on Jan. 5, 2012.

(51) Int. Cl.
  *C07D 401/06*   (2006.01)
  *C07D 209/10*   (2006.01)
  *C07D 209/14*   (2006.01)

(52) U.S. Cl.
  CPC .......... *C07D 209/10* (2013.01); *C07D 209/14* (2013.01); *C07D 401/06* (2013.01)

(58) Field of Classification Search
  CPC ........................... C07D 209/10; C07D 401/06
  USPC .. 514/323, 339, 415; 546/201, 277; 548/506
  See application file for complete search history.

(56) References Cited

U.S. PATENT DOCUMENTS

| | | | |
|---|---|---|---|
| 7,820,144 B2 * | 10/2010 | Makriyannis et al. | 424/9.37 |
| 8,642,660 B2 * | 2/2014 | Goldfarb | 514/641 |
| 2010/0063050 A1 * | 3/2010 | Makriyannis et al. | 514/236.5 |

OTHER PUBLICATIONS

Merchant et al. "Heterocyclic compounds . . . " CA75:118189 (1971).*
ZINC02708455 Pubchem p. 1-5 (2009).*
ZINC12139853 Pubchem p. 1-15 (2009).*
Barange et al. "Facile and highly efficient . . . " Tetrahedron Lett. 50, 5116-9 (2009).*
Barange et al. "facile and . . . " CA151:380969.*
Goldfarb et al. "Method using lifespan . . . " CA151:92844 (2009).*
Improper Markush, Fed. Reg. 76(27) p. 7162-7175, slide 1, 64-67 (2011).*
Isostere, Wikipedia p. 1, (2015).*
Lee et al. "Pharmaceutical composition . . . " CA149:283032 (2008).*
Praveen et al. "Efficient synthesis . . . " Tetrhedron 65, 9244-9255 (2009).*
Praveen et al. "Efficient synthesis . . . " CA152:12074 (2005).*
Substituted tryptamine, Wikipedia p. 1-8 (2015).*
Bandini et al. "Catalytic enantioselective . . . " Chrality 17, p. 522-29 (2005).*
Bandini et al. "Catalytic . . . " CA145:45873 (2005).*
Patani et al. "Bioisosterism: a . . . " Chem. Rev. 86, 3147-3176 (1996).*
Forbes et al. "N-(1-methyl . . . " J. Med. Chem. 36, 1104-1107 (1993).*
Saunders et al. "addiction medicine" p. 388 (2016).*
Berge, et al., "Pharmaceutical Salts," J. Pharm. Sci., vol. 66, pp. 1-19 (1977).
Database Registry [Online], Chemical Abstracts Service, Columbus, Ohio, US; Aug. 9, 2002, XP002743011; Database Accession No. 443329-59-7 (1 pg.).
Database Registry [Online], Chemical Abstracts Service, Columbus, Ohio, US; Dec. 13, 2000, XP002743018; Database Accession No. 308298-24-0, 308294-77-1 (2 pg.).
Database Registry [Online], Chemical Abstracts Service, Columbus, Ohio, US; Dec. 28, 2001, XP002743013; Database Accession No. 379252-68-3, 379252-67-2 (2 pg.).
Database Registry [Online], Chemical Abstracts Service, Columbus, Ohio, US; Dec. 8, 2000, XP002743019; Database Accession No. 307543-40-4, 307540-46-1 (2 pg.).
Database Registry [Online], Chemical Abstracts Service, Columbus, Ohio, US; Jan. 17, 2001, XP002743017; Database Accession No. 314257-89-1, 314257-88-0, 314257-87-9, 314257-86-8, 314257-89-7, 314257-84-6 (6pg.).
Database Registry [Online], Chemical Abstracts Service, Columbus, Ohio, US; Jan. 19, 2001, XP002743016; Database Accession No. 325240-33-6, 315240-17-6, 315239-89-5, 315239-88-4, 315235-07-5, 315235-06-4, 315235-05-3, 315235-04-2, 315235-03-1, 315234-75-4, 315234-69-6 (11 pg.).
Database Registry [Online], Chemical Abstracts Service, Columbus, Ohio, US; Jan. 3, 2002, XP002743012; Database Accession No. 380352-72-7, 380352-52-3, 380352-24-9 (3 pg.).
Database Registry [Online], Chemical Abstracts Service, Columbus, Ohio, US; Mar. 4, 2001, XP002743015; Database Accession No. 325474-02-0, 325474-01-9 (2 pg.).
Database Registry [Online], Chemical Abstracts Service, Columbus, Ohio, US; Mar. 7, 2001, XP002743014; Database Accession No. 325992-84-5, 325992-82-3, 325992-80-1 (3 pg.).
Database Registry [Online], Chemical Abstracts Service, Columbus, Ohio, US; Nov. 16, 2000, XP002743020; Database Accession No. 303035-70-3 (1 pg.).

(Continued)

Primary Examiner — Celia Chang
(74) Attorney, Agent, or Firm — Posternak Blankstein & Lund LLP

(57) ABSTRACT

The present invention relates to novel heterocyclic derivatives which are allosteric modulators of cannabinoid receptor 1 (CB1) and which are useful for the treatment or prevention of neurological and psychiatric disorders associated with endocannabinoid dysfunction and diseases in which the CB1 subtype of cannabinoid receptor is involved; to processes for their preparation; to pharmaceutical compositions comprising them; and to methods of using them.

7 Claims, 3 Drawing Sheets

(56) References Cited

OTHER PUBLICATIONS

Database Registry [Online], Chemical Abstracts Service, Columbus, Ohio, US; Sep. 4, 2002, XP002743010; Database Accession No. 446270-67-3 (1 pg.).
Database Registry [Online], Chemical Abstracts Service, Columbus, Ohio, US; Sep. 5, 2002, XP002742629; Database Accession No. 446826-78-4 (1 pg.).
Dupeyre, et al., "A One-pot Synthesis of 7-Phenylindolo [3,2-a] Carbazoles from Indoles and [beta]-nitostyrenes, via an Unprecedented Reaction Sequence," Organic & Biomolecular Chemistry, vol. 9, No. 22, pp. 7780-7790 (2011).
Extended European Search Report issued by the European Patent Office for European Patent Application No. 13733561.8 dated Aug. 12, 2015 (13 pgs.).
Gao, et al., "General and Efficient Strategy for Erythrinan and Homoerythrinan Alkaloids: Syntheses of (±)-3-Demethoxyerythratidinone and (±)-Erysotramidine," Org. Lett., vol. 8(11), pp. 2373-2376 (2006).
Habib, et al., "Catalyst Free Conjugate Addition of Indoles and Pyrroles to Nitro Alkenes Under Solvent Free Condition (SFC): an Effective Greener Route to Access 3-(2-nitro-1-phenylethyl)-1H-indole and 2-(2-nitro-1-phenylethyl)-1H-pyrrole Derivatives," Tetrahedron, Elsevier Science Publishers, Amsterdam, NL, vol. 66, No. 34, pp. 7050-7056 (Aug. 21, 2010).
International Search Report and Written Opinion issued by the U.S. Patent and Trademark Office as International Searching Authority for International Application No. PCT/US2013/020543 mailed Mar. 12, 2013 (10 pgs.).
Kapur, et al., "Mutation Studies of Ser7.39 and Ser2.60 in the Human CB1 Cannabinoid Receptor: Evidence for a Serine-Induced Bend in CB1 Transmembrane Helix 7," Mol Pharmacol, vol. 71, pp. 1512-1524 (2007).
Kilic, et al., "Synthesis of Highly-substituted Indole Library via Conjugate Additions of Indoline and their Synthetic Tool Potentials," Tetrahedron, Elsevier Science Publishers, Amsterdam, NL, vol. 68, No. 27, pp. 5619-5630 (Apr. 16, 2012).
Lipczynska-Kochany, et al., "Intramolecular Hudrogen Bond in Some Secondary and Tertiary Aliphatic B-Nitroalcholos," Bulletin de l'Academie Polonaise des Sciences, Serie des Sciences Chimiques, vol. 24, pp. 513-518 (1977).
Lancianesi, et al., "Synthesis and Funcitonalization of Unsymmetrical Arylsulfonyl Bisindoles and Bisbenzazoles," Advanced Synthesis & Catalysis, vol. 354, No. 18, pp. 3539-3544 (Dec. 14, 2012).
Lopchuk, J.M. and Gribbel, G.W., "A convenient 1,3-dipolar cycloaddition approach to pyridylpyrroles," Tetrahedron Letters, vol. 52, Issue 32, pp. 4106-4108 (2011).
Marvel, C.S. and Lycan, W. H., "Nitrostyrene" Org. Synth., Coll. vol. 1, 413 (1941); vol. 9, pp. 66 (1929) (4 total pages).
Ramesh, et al., "An Unprecedented Route for the Sybthesis of 3,3'-Biindoles by Reductive Cyclization of 3-[2-Nitro-1-(2-nitrophenyl)ethyl]-1H-indoles Mediated by Iton/Acetic Acid," European Journal of Organic Chemistry, vol. 2010, No. 20, pp. 3796-3801 (Jul. 9, 2010).
Salgar, et al., "Studies in Heterocyclic Compounds. III. Reaction of Indoles with Dienophiles," Journal Fur Praktische Chemie, vol. 14, No. 1-2, pp. 108-112 (1961).
Tarnus, et al., "3-Amino-2-hydroxy-propionaldehyde and 3-amino-1-hydroxy-propan-2-one derivatives: new classes of aminopeptidase inhibitors," Bioorganic & Medicinal Chemistry, vol. 4, Issue 8, pp. 1287-1297 (Aug. 1996).
Yang, et al., "Cyanuric Chloride-Catalyzed Michael Addition of Indoles to Nitroolefins under Solvent-Free Conditions," Journal of Chemistry, vol. 22, No. 8, 6 pages (Jan. 2013).
Noland, W.E. and Lange, R.F., The Nitroethylation of Indoles. III.[1-3] A Synthetic Route to Substitute Tryptamines, Journal of the American Chemical Society, vol. 81, pp. 1203-1209 (1959).
De Rosa, M. and Soriente, A., "A Combination of Water and Microwave Irradiation Promotes the Catalyst-free Addition of Pyrroles and Indoles to Nitroalkenes," Tetrahedron, vol. 66, No. 16, pp. 2981-2986 (2010).
Gu, et al., "Glycerl as an Efficient Promoting Medium for Organic Reactions," Advanced Synthesis and Catalysis, vol. 350, No. 13, pp. 2007-2012 (2008).
Hari, et al., "Silica sulfuric Acid-catalyzed Friedel-Crafts Alkylation of Indoles with Nitro Olefins," Synthetic Communications, vol. 38; No. 1, pp. 100-105 (2008).
Wu, et al., "A New Type of Bis(sulfonamide)-Diamine Ligand for a Cu(OTf)$_2$-Catalyzed Asymmetric FriedelCrafts Alkylation Reaction of Indoles with Nitroalkenes," Organic Letters, vol. 13, No. 18, pp. 4834-4837 (2011).

* cited by examiner

ALLOSTERIC MODULATORS OF CB1 CANNABINOID RECEPTORS

CROSS REFERENCE TO RELATED APPLICATION

This application is a continuation of International Application No. PCT/US2013/020543 (International Publication No. WO 2013/103967), which was filed on Jan. 7, 2013, and which claims the benefit of U.S. Provisional Application Patent No. 61/583,380, filed Jan. 5, 2012. The entire contents of both applications are hereby incorporated by reference herein.

FIELD

The present application relates to heterocyclic derivatives which are allosteric modulators (positive allosteric modulators, allosteric agonists, ago-allosteric modulators) of cannabinoid receptor 1 (CB1) and are useful for the treatment or prevention of neurological and psychiatric disorders associated with endocannabinoid dysfunction and diseases in which the CB1 subtype of cannabinoid receptor is involved. The present application is also directed to pharmaceutical compositions comprising these compounds and the use of these compounds and compositions in the prevention or treatment of such diseases in which cannabinoid receptors are involved such as pain, neuropathic pain, GI disorders, glaucoma, drug addiction, eating disorders (anorexia nervosa; bulimia nervosa; binge-eating disorders) and post-traumatic stress disorders (PTSD).

BACKGROUND OF THE INVENTION

Direct acting CB1 agonists have been used for the treatment or prevention of neurological and psychiatric disorders associated with endocannabinoid dysfunction and diseases in which the CB1 subtype of cannabinoid receptor is involved. However, they suffer from disadvantages such as addiction, abuse potential as well as tolerance associated with their use.

Anorexia nervosa (AN) is a major psychiatric eating disorder associated with substantial morbidity and mortality and its characteristic symptoms include the refusal to maintain a minimally normal body weight, an intense fear of becoming fat, and a disturbed perception of body shape and size. It is also characterized by anhedonia whereby patients experience little pleasure or reward in many aspects of their lives. Pharmacotherapeutic interventions for treatment of AN are extremely limited, as there is still a lack of understanding of their pathogenesis. The endocannabinoid system has been recently recognized as an important target in both reward processing and feeding behavior. Studies in AN patients have linked AN associated disorder attitudes and behavior to a dysfunctional endocannabinoid system. In recently concluded studies, THC, a cannabinoid receptor agonist was shown to attenuate weight loss in a rodent model of activity-based anorexia. Although use of a direct-acting CB1 receptor agonist for treating AN associated anhedonia and weight loss seems an attractive pharmacotherapeutic approach, its use may lead to addiction.

Accomplishing CB1 agonism with a different pharmacological mechanism may represent a safer alternative. One promising alternative approach is the development of positive allosteric modulators (PAMs) of CB1 receptors which, by binding to a sub-type-specific and topographically distinct site from the orthosteric pocket, would potentiate the action of endocannabinoids and thus act more selectively to tune CB signaling in a site- and event-specific fashion.

Highly CB1 selective modulators with a minimal propensity to produce adverse effects would be desirable. Moreover, it would be desirable to identify types of modulators which are brain-permeable, functionally potent modulators (cAMP) and likely devoid of abuse potential.

SUMMARY OF THE INVENTION

The present invention is directed to compositions and methods that can be used for the treatment of these disorders while minimizing or eliminating abuse potential and providing higher specificity with reduced side effects. The present invention relates to heterocyclic derivatives which are allosteric modulators of cannabinoid receptor 1 (CB1) and which are useful for the treatment or prevention of neurological and psychiatric disorders associated with endocannabinoid dysfunction and diseases in which the CB1 subtype of cannabinoid receptor is involved. The invention is also directed to pharmaceutical compositions comprising these compounds and the use of these compounds and compositions in the prevention or treatment of such diseases in which cannabinoid receptors are involved such as pain, neuropathic pain, glaucoma, drug addiction, eating disorders (anorexia nervosa; bulimia nervosa; binge-eating disorders) and post-traumatic stress disorders.

In one aspect, the present invention provides a compound having the following structure, or a pharmaceutically acceptable salt thereof:

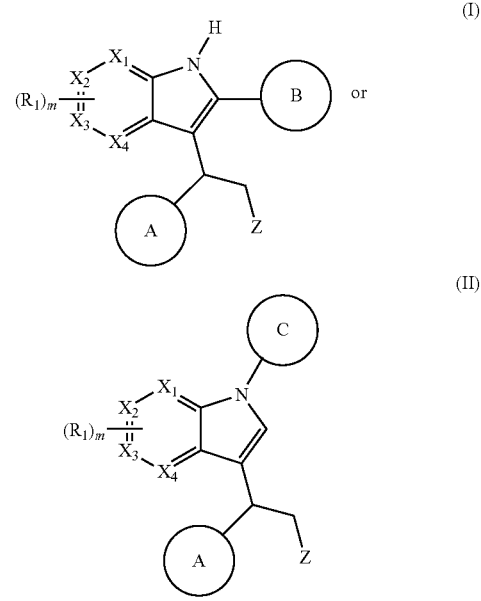

wherein each of each of rings A, B and C is independently a substituted or unsubstituted carbocyclic ring, bicyclic ring, aromatic ring, or heterocyclic ring;
each $X_1$, $X_2$, $X_3$ and $X_4$ is C or one of $X_1$, $X_2$, $X_3$ and $X_4$ may be N;
Z is $NO_2$ or CN;
each R1 is independently H, halogen, OH, CN, ($C_1$-$C_6$) alkyl, ($C_2$-$C_6$)alkenyl, ($C_2$-$C_6$) alkynyl, ($C_1$-$C_6$) alkoxy, ($C_3$-$C_7$) cycloalkyl, ($C_1$-$C_6$) alkylthio, $NR_aR_b$, $R_aR_b$ or haloalkyl (e.g., $CF_3$); each occurrence of $R_a$ and $R_b$ is independently hydrogen or $(C_1-C_6)$alkyl, or $R_a$ and $R_b$, form a saturated or unsaturated heterocyclic ring containing from three to seven ring atoms, which ring may optionally contain another heteroatom selected from the group consisting of nitrogen, oxygen and sulfur and may be optionally substituted by from one to three groups which may be the same or different selected from the group consisting of $(C_1-C_4)$alkyl, phenyl and benzyl; and m is 1-4; provided the compound of structure I is not:

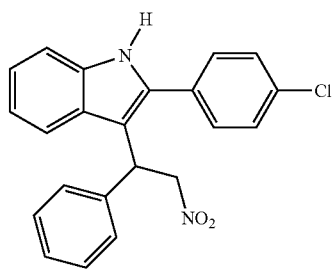

2-(4-chlorophenyl)-3-(2-nitro-1-phenylethyl)-1H-indole or

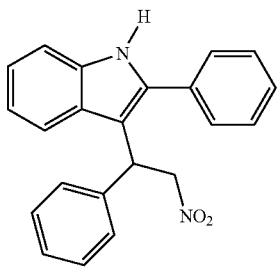

3-(2-nitro-1-phenylethyl)-2-phenyl-1H-indole

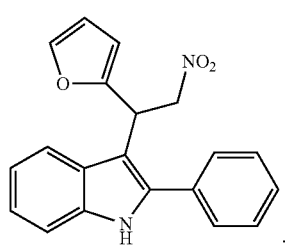

.

In accordance with another aspect, the present invention provides a compound having the following structure, or a pharmaceutically acceptable salt thereof:

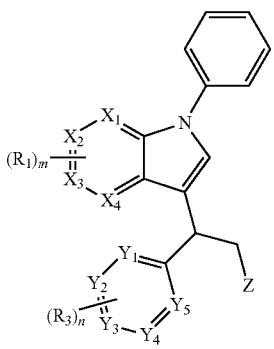 (IA)

or (IIA)

wherein each of $X_1$, $X_2$, $X_3$ and $X_4$ is C or one of $X_1$, $X_2$, $X_3$ and $X_4$ may be N;
each of $Y_1$, $Y_2$, $Y_3$, $Y_4$ and $Y_5$ is C or one of $Y_1$, $Y_2$, $Y_3$, $Y_4$ and $Y_5$ may be N;
Z is $NO_2$ or CN;
each $R_1$, $R_2$ and $R_3$ is independently H, halogen, OH, CN, $(C_1-C_6)$alkyl, $(C_2-C_6)$alkenyl, $(C_2-C_6)$ alkynyl, $(C_1-C_6)$ alkoxy, $(C_3-C_7)$ cycloalkyl, $(C_1-C_6)$ alkylthio, $NR_aR_b$, $R_aR_b$ or haloalkyl (e.g., $CF_3$);
each occurrence of $R_a$ and $R_b$ is independently hydrogen or $(C_1-C_6)$alkyl, or $R_a$ and $R_b$, form a saturated or unsaturated heterocyclic ring containing from three to seven ring atoms, which ring may optionally contain another heteroatom selected from the group consisting of nitrogen, oxygen and sulfur and may be optionally substituted by from one to three groups which may be the same or different selected from the group consisting of $(C_1-C_4)$alkyl, phenyl and benzyl;
n is 1-5; and
m is 1-4; provided the compound of structure 1 is not:

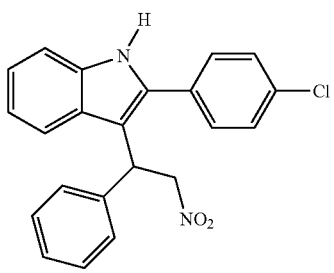

2-(4-chlorophenyl)-3-(2-nitro-1-phenylethyl)-1H-indole or

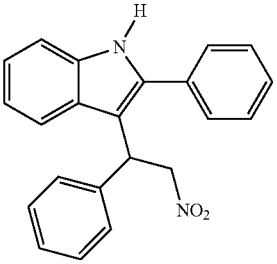

3-(2-nitro-1-phenylethyl)-2-phenyl-1H-indole.

In another aspect, the present invention provides a pharmaceutical composition comprising at least one compound as described herein and a pharmaceutically-acceptable carrier or diluent.

In yet another aspect, the present invention provides a method for treating or preventing a neurological or psychi-

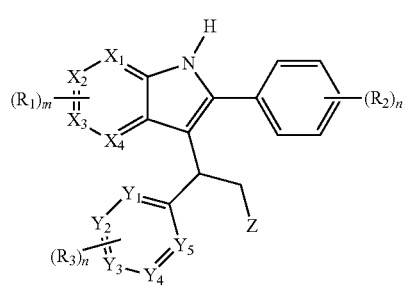

atric disorder in a mammalian species in need thereof, the method comprising administering to the mammalian species a therapeutically effective amount of at least one compound as described herein, wherein the disorder is selected from a disease or disorder in which the cannabinoid receptors are involved.

In yet another aspect, the present invention provides a method for treating a disorder associated with endocannabinoid dysfunction in a mammalian species in need thereof, the method comprising administering to the mammalian species a therapeutically effective amount of at least one compound as described herein, wherein the disorder is selected from eating disorders and post-traumatic stress disorder.

In a further aspect, the present invention provides a method for treating an eating disorder in a mammalian species in need thereof, the method comprising administering to the mammalian species a therapeutically effective amount of at least one compound as described herein, wherein the eating disorder is selected from anorexia nervosa and bulimia nervosa.

DETAILED DESCRIPTION OF THE INVENTION

Definitions

Figure 1:
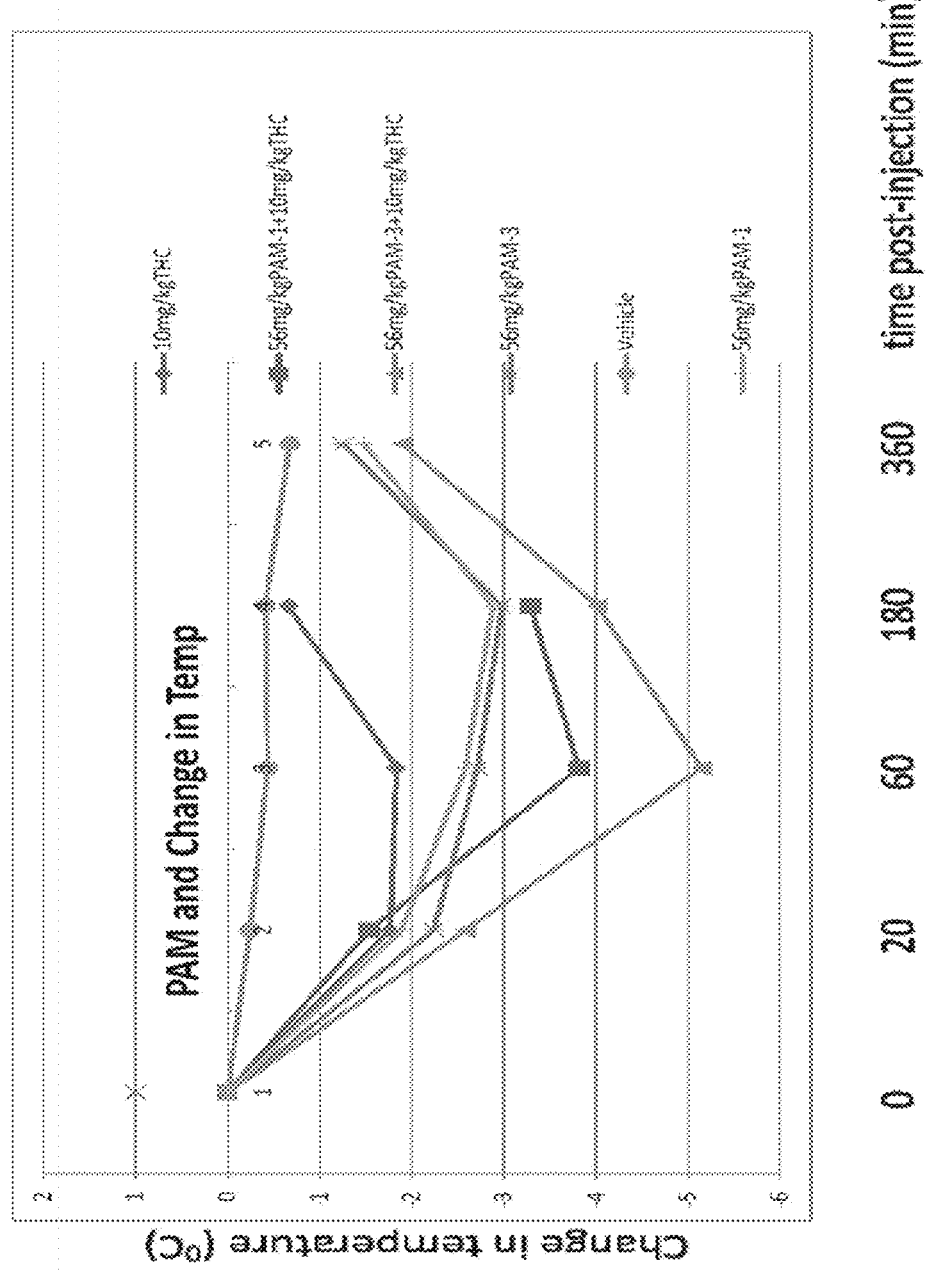
FIG. 1. is a graph of change in temperature as a function of post-injection time for various CB1 PAMs.

The following are definitions of terms used in the present specification. The initial definition provided for a group or term herein applies to that group or term throughout the present specification individually or as part of another group, unless otherwise indicated.

The terms "alkyl" and "alk" refer to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "($C_1$-$C_4$) alkyl" refers to a straight or branched chain alkane (hydrocarbon) radical containing from 1 to 4 carbon atoms, such as methyl, ethyl, propyl, isopropyl, n-butyl, t-butyl, and isobutyl. The term "($C_1$-$C_6$)alkyl" refers to a straight or branched chain alkane (hydrocarbon) radical containing from 1 to 6 carbon atoms, such as n-hexyl, 2-methylpentyl, 3-methylpentyl, 4-methylpentyl, 2,3-dimethylbutyl, 2,2-dimethylbutyl, in addition to those exemplified for "($C_1$-$C_4$)alkyl." "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $Cl_3$), cyano, nitro, oxo (i.e., $=O$), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_e$, $NR_bS(=O)_2R_e$, $NR_bP(=O)_2R_e$, $S(=O)_2NR_bR_e$, $P(=O)_2NR_bR_e$, $C(=O)OR_d$, $C(=O)R_a$, $C(=O)NR_bR_e$, $OC(=O)R_a$, $OC(=O)NR_bR_e$, $NR_bC(=O)OR_e$, $NR_dC(=O)NR_bR_e$, $NR_dS(=O)_2NR_bR_e$, $NR_dP(=O)_2NR_bR_e$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. In the aforementioned exemplary substitutents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplaries of such groups include ethenyl or allyl. The term "$C_2$-$C_6$ alkenyl" refers to a straight or branched chain hydrocarbon radical containing from 2 to 6 carbon atoms and at least one carbon-carbon double bond, such as ethylenyl, propenyl, 2-propenyl, (E)-but-2-enyl, (Z)-but-2-enyl, 2-methy(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. "Substituted alkenyl" refers to an alkenyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $Cl_3$), cyano, nitro, oxo (i.e., $=O$), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substitutents can themselves be optionally substituted.

The term "alkynyl" refers to a straight or branched chain hydrocarbon radical containing from 2 to 12 carbon atoms and at least one carbon to carbon triple bond. An exemplary of such groups includes ethynyl. The term "$C_2$-$C_6$ alkynyl" refers to a straight or branched chain hydrocarbon radical containing from 2 to 6 carbon atoms and at least one carbon-carbon triple bond, such as ethynyl, prop-1-ynyl, prop-2-ynyl, but-1-ynyl, but-2-ynyl, pent-1-ynyl, pent-2-ynyl, hex-1-ynyl, hex-2-ynyl, hex-3-ynyl. "Substituted alkynyl" refers to an alkynyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $Cl_3$), cyano, nitro, oxo (i.e., $=O$), $CF_3$, OCF3, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted.

The term "cycloalkyl" refers to a fully saturated cyclic hydrocarbon group containing from 1 to 4 rings and 3 to 8 carbons per ring. "$C_3$-$C_7$ cycloalkyl" refers to cyclopropyl, cyclobutyl, cyclopentyl, cyclohexyl, or cycloheptyl. "Substituted cycloalkyl" refers to a cycloalkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_e$, $NR_bS(=O)_2R_e$, $NR_bP(=O)_2R_e$, $S(=O)_2NR_bR_e$, $P(=O)_2NR_bR_e$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include spiro-attached or fused cyclic substitutents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substitutents can themselves be optionally substituted.

The term "cycloalkenyl" refers to a partially unsaturated cyclic hydrocarbon group containing 1 to 4 rings and 3 to 8 carbons per ring. Exemplaries of such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_e$, $NR_bS(=O)_2R_e$, $NR_bP(=O)_2R_e$, $S(=O)_2NR_bR_e$, $P(=O)_2NR_bR_e$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substitutents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_e$, $NR_bS(=O)_2R_e$, $NR_bP(=O)_2R_e$, $S(=O)_2NR_bR_e$, $P(=O)_2NR_bR_e$, $C(=O)OR_d$, $C(=O)R_a$, $C(=O)NR_bR_e$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include fused cyclic groups, especially fused cycloalkyl, fused cycloalkenyl, fused heterocycle, or fused aryl, where the aforementioned cycloalkyl, cycloalkenyl, heterocycle and aryl substitutents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_bS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include spiro-attached or fused cyclic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "alkylamino" refers to a group having the structure —NHR', wherein R' is hydrogen, alkyl or substituted alkyl, cycloalkyl or substituted cycloalkyl, as defined herein. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each independently alkyl or substituted alkyl, cycloalkyl or substituted cycloalkyl, cycloalkenyl or substituted cyclolalkenyl, aryl or substituted aryl, heterocylyl or substituted heterocyclyl, as defined herein. R and R' may be the same or different in an dialkyamino moiety. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

The terms "halogen" or "halo" refer to chlorine, bromine, fluorine or iodine.

Unless otherwise indicated, any heteroatom with unsatisfied valences is assumed to have hydrogen atoms sufficient to satisfy the valences.

The compounds of the present invention may form salts which are also within the scope of this invention. Reference to a compound of the present invention is understood to include reference to salts thereof, unless otherwise indicated. The term "salt(s)," as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of a compound of the present invention may be formed, for example, by reacting a compound I with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

Compounds of the present invention which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the invention are also contemplated herein. The term "prodrug" as employed herein denotes a compound that, upon administration to a subject, undergoes chemical conversion by metabolic or chemical processes to yield a compound of the present invention, or a salt and/or solvate thereof. Solvates of the compounds of the present invention include, for example, hydrates.

Compounds of the present invention, and salts or solvates thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 90%, for example, equal to greater than 95%, equal to or greater than 99% pure ("substantially pure" compound I), which is then used or formulated as described herein. Such "substantially pure" compounds of the present invention are also contemplated herein as part of the present invention.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in "Organic Chemistry," Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

The present invention also includes isotopically labeled compounds, which are identical to the compounds disclosed herein, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2$H, $^3$H, $^{13}$C, $^{11}$C, $^{14}$C, $^{15}$N, $^{18}$O, $^{17}$O, $^{31}$P, $^{32}$P, $^{35}$S, $^{18}$F, r and $^{36}$Cl, respectively. Compounds of the present invention, or an enantiomer, diastereomer, tautomer, or pharmaceutically acceptable salt or solvate thereof, which contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds can generally be prepared by carrying out the procedures disclosed in the Schemes and/or in the Examples below, by substituting a readily available isotopically labeled reagent for a non-isotopically labeled reagent.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Compounds

The compounds of the present disclosure are allosteric modulators of CB1 cannabinoid receptors.

In one aspect, the present invention provides a compound having the following structure, or a pharmaceutically acceptable salt thereof:

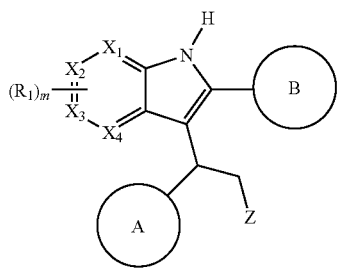

(I)

or

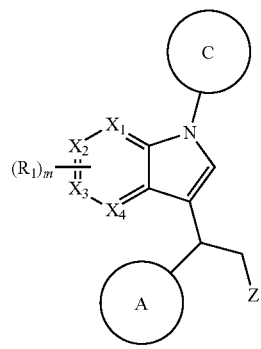

(II)

wherein each of each of rings A, B and C is independently a substituted or unsubstituted carbocyclic ring, bicyclic ring, aromatic ring, or heterocyclic ring;

each $X_1$, $X_2$, $X_3$ and $X_4$ is C or one of $X_1$, $X_2$, $X_3$ and $X_4$ may be N;

Z is $NO_2$ or CN;

each R1 is independently H, halogen, OH, CN, $(C_1-C_6)$ alkyl, $(C_2-C_6)$alkenyl, $(C_2-C_6)$ alkynyl, $(C_1-C_6)$ alkoxy, $(C_3-C_7)$ cycloalkyl, $(C_1-C_6)$ alkylthio, $NR_aR_b$, $R_aR_b$ or haloalkyl (e.g., $CF_3$); each occurrence of $R_a$ and $R_b$ is independently hydrogen or $(C_1-C_6)$alkyl, or $R_a$ and $R_b$, form a saturated or unsaturated heterocyclic ring containing from three to seven ring atoms, which ring may optionally contain another heteroatom selected from the group consisting of nitrogen, oxygen and sulfur and may be optionally substituted by from one to three groups which may be the same or different selected from the group consisting of $(C_1-C_4)$alkyl, phenyl and benzyl; and m is 1-4; provided the compound of structure I is not:

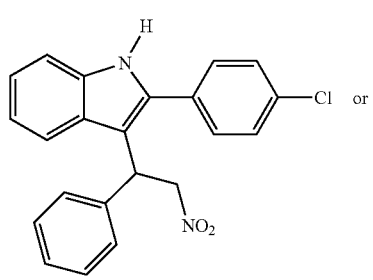

2-(4-chlorophenyl)-3-(2-nitro-1-phenylethyl)-1H-indole

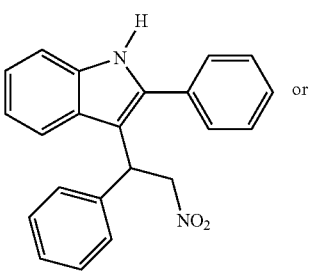

3-(2-nitro-1-phenylethyl)-2-phenyl-1H-indole

-continued

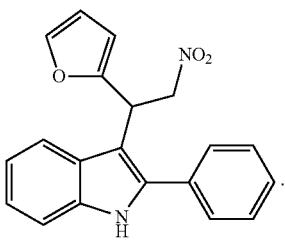

In accordance with another aspect, the present invention provides a compound having the following structure, or a pharmaceutically acceptable salt thereof:

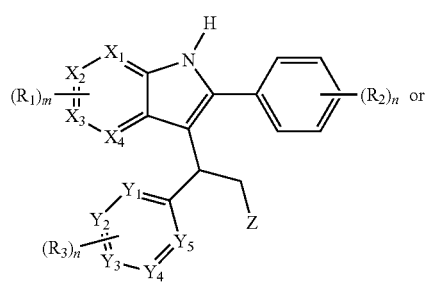
(IA)

(IIA)

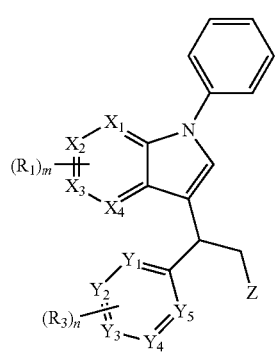

wherein each of $X_1$, $X_2$, $X_3$ and $X_4$ is C or one of $X_1$, $X_2$, $X_3$ and $X_4$ may be N; each of $Y_1$, $Y_2$, $Y_3$, $Y_4$ and $Y_5$ is C or one of $Y_1$, $Y_2$, $Y_3$, $Y_4$ and $Y_5$ may be N;

Z is $NO_2$ or CN;

each $R_1$, $R_2$ and $R_3$ is independently H, halogen, OH, CN, $(C_1-C_6)$alkyl, $(C_2-C_6)$alkenyl, $(C_2-C_6)$ alkynyl, $(C_1-C_6)$ alkoxy, $(C_3-C_7)$ cycloalkyl, $(C_1-C_6)$ alkylthio, $NR_aR_b$, $R_aR_b$ or haloalkyl (e.g., $CF_3$);

each occurrence of $R_a$ and $R_b$ is independently hydrogen or $(C_1-C_6)$alkyl, or $R_a$ and $R_b$, form a saturated or unsaturated heterocyclic ring containing from three to seven ring atoms, which ring may optionally contain another heteroatom selected from the group consisting of nitrogen, oxygen and sulfur and may be optionally substituted by from one to three groups which may be the same or different selected from the group consisting of $(C_1-C_4)$alkyl, phenyl and benzyl;

n is 1-5; and m is 1-4; provided the compound of structure 1 is not:

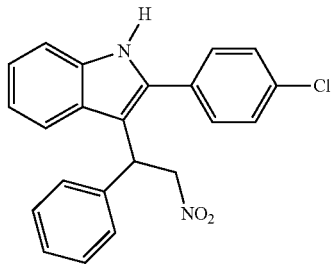

2-(4-chlorophenyl)-3-
(2-nitro-1-phenylethyl)-1H-indole or

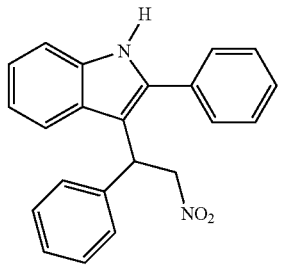

3-(2-nitro-1-phenylethyl)-2-
phenyl-1H-indole

.

In accordance with another aspect, the present invention is directed to a compound having the following structure, or a pharmaceutically acceptable salt thereof:

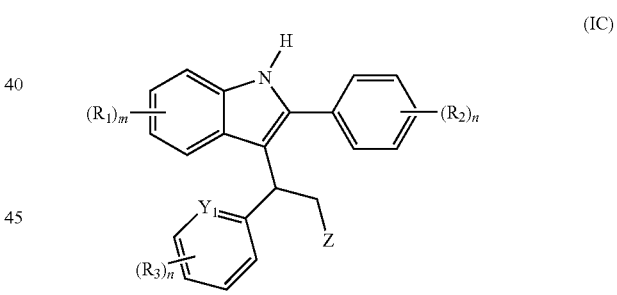
(IC)

wherein $Y_1$ is C or N;

Z is $NO_2$ or CN;

each $R_1$, $R_2$ and $R_3$ is independently H, halogen, OH, CN, $(C_1-C_6)$alkyl, $(C_2-C_6)$ alkenyl, $(C_2-C_6)$ alkynyl, $(C_1-C_6)$ alkoxy, $(C_3-C_7)$ cycloalkyl, $(C_1-C_6)$ alkylthio, $NR_aR_b$, $R_aR_b$ or haloalkyl (e.g., $CF_3$);

each occurrence of $R_a$ and $R_b$ is independently hydrogen or $(C_1-C_6)$alkyl, or $R_a$ and $R_b$, form a saturated or unsaturated heterocyclic ring containing from three to seven ring atoms, which ring may optionally contain another heteroatom selected from the group consisting of nitrogen, oxygen and sulfur and may be optionally substituted by from one to three groups which may be the same or different selected from the group consisting of $(C_1-C_4)$alkyl, phenyl and benzyl;

n is 1-5; and m is 1-4; provided the compound of structure 1 is not:

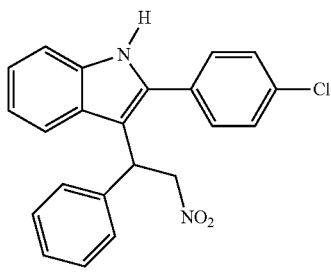

2-(4-chlorophenyl)-3-
(2-nitro-1-phenylethyl)-1H-indole       or

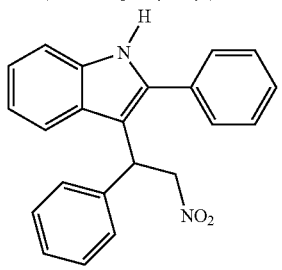

3-(2-nitro-1-phenylethyl)-2-
phenyl-1H-indole         .

In certain embodiments, the present invention provides one of the following compounds:

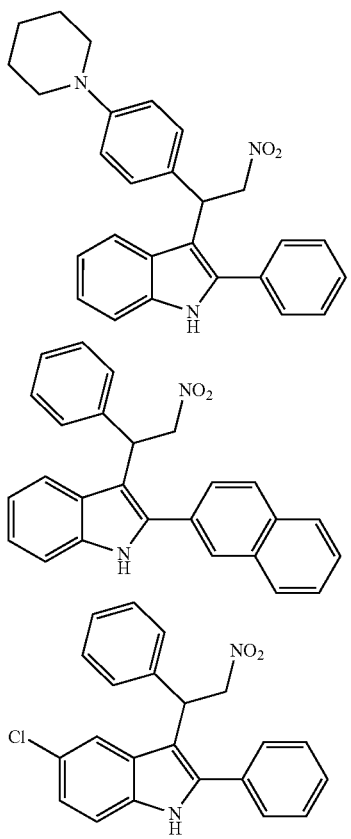

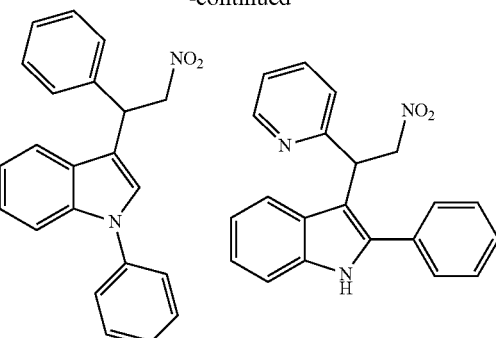

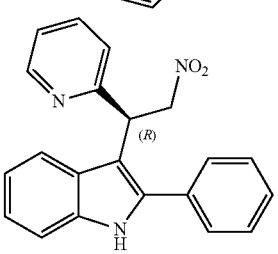

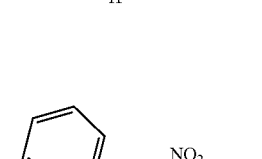

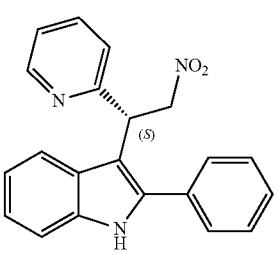

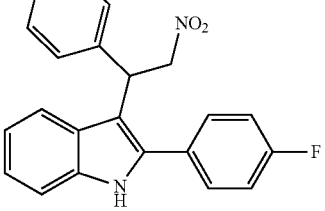

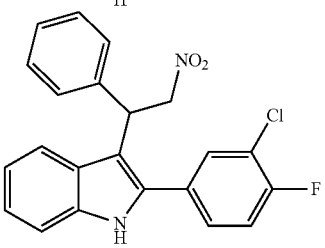

In another aspect, the present invention provides a pharmaceutical composition comprising at least one compound as described herein and a pharmaceutically-acceptable carrier or diluent.

Compounds useful as CB1 positive allosteric modulators in pharmaceutical compositions include compounds having the following structure, or a pharmaceutically acceptable salt thereof:

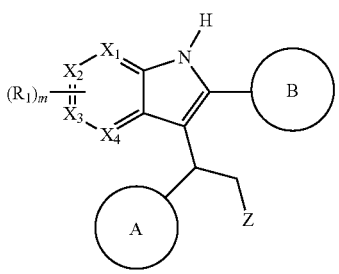

(I)

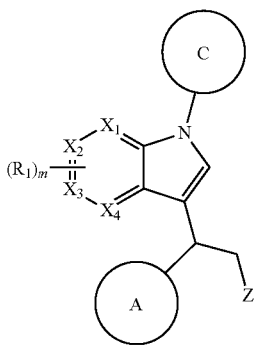

(II)

wherein each of each of rings A, B and C is independently a substituted or unsubstituted carbocyclic ring, bicyclic ring, aromatic ring, or heterocyclic ring;

each $X_1$, $X_2$, $X_3$ and $X_4$ is C or one of $X_1$, $X_2$, $X_3$ and $X_4$ may be N;

Z is $NO_2$ or CN;

each $R_1$ is independently H, halogen, OH, CN, $(C_1-C_6)$alkyl, $(C_2-C_6)$alkenyl, $(C_2-C_6)$ alkynyl, $(C_1-C_6)$ alkoxy, $(C_3-C_7)$ cycloalkyl, $(C_1-C_6)$ alkylthio, $NR_aR_b$, $R_aR_b$ or haloalkyl (e.g., $CF_3$); each occurrence of $R_a$ and $R_b$ is independently hydrogen or $(C_1-C_6)$alkyl, or $R_a$ and $R_b$, form a saturated or unsaturated heterocyclic ring containing from three to seven ring atoms, which ring may optionally contain another heteroatom selected from the group consisting of nitrogen, oxygen and sulfur and may be optionally substituted by from one to three groups which may be the same or different selected from the group consisting of $(C_1-C_4)$alkyl, phenyl and benzyl; and m is 1-4; provided the compound of structure I is not:

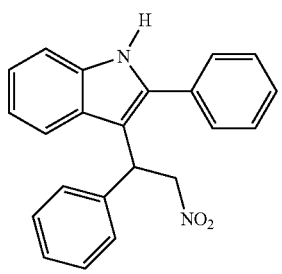

3-(2-nitro-1-phenylethyl)-2-phenyl-1H-indole or

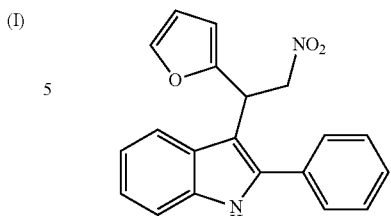

In accordance with particular embodiments, the present invention provides compounds useful as CB1 positive allosteric modulators in pharmaceutical compositions. Examples of these compounds include those having the following structure, or a pharmaceutically acceptable salt thereof:

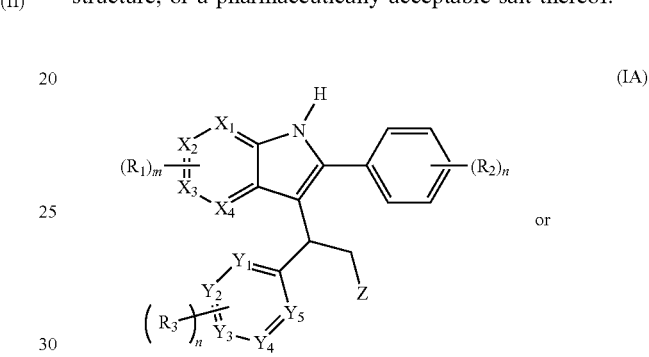

(IA)

or (IIA)

wherein each of $X_1$, $X_2$, $X_3$ and $X_4$ is C or one of $X_1$, $X_2$, $X_3$ and $X_4$ may be N;

each of $Y_1$, $Y_2$, $Y_3$, $Y_4$ and $Y_5$ is C or one of $Y_1$, $Y_2$, $Y_3$, $Y_4$ and $Y_5$ may be N;

Z is $NO_2$ or CN;

each $R_1$, $R_2$ and $R_3$ is independently H, halogen, OH, CN, $(C_1-C_6)$alkyl, $(C_2-C_6)$alkenyl, $(C_2-C_6)$ alkynyl, $(C_1-C_6)$ alkoxy, $(C_3-C_7)$ cycloalkyl, $(C_1-C_6)$ alkylthio, $NR_aR_b$, $R_aR_b$ or haloalkyl (e.g., $CF_3$);

each occurrence of $R_a$ and $R_b$ is independently hydrogen or $(C_1-C_6)$alkyl, or $R_a$ and $R_b$, form a saturated or unsaturated heterocyclic ring containing from three to seven ring atoms, which ring may optionally contain another heteroatom selected from the group consisting of nitrogen, oxygen and sulfur and may be optionally substituted by from one to three groups which may be the same or different selected from the group consisting of $(C_1-C_4)$alkyl, phenyl and benzyl;

n is 1-5; and
m is 1-4; provided the compound of structure 1 is not:
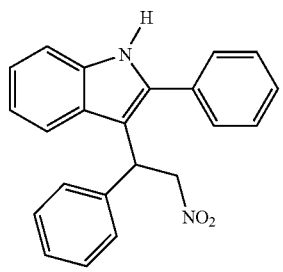
3-(2-nitro-1-phenylethyl)-2-phenyl-1H-indole.
In certain embodiments, the present invention provides pharmaceutical compositions containing one of the following compounds:
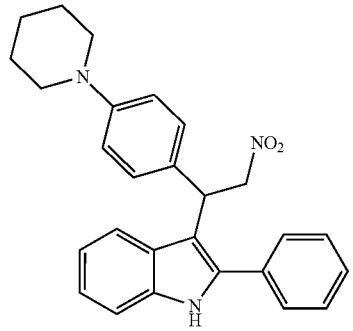
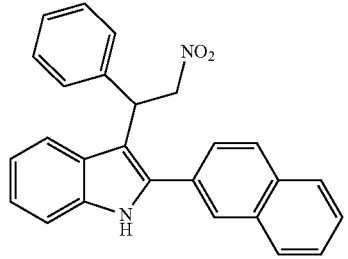
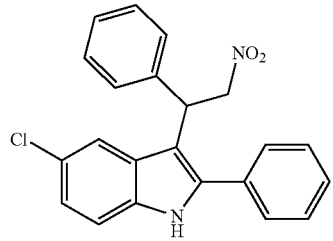
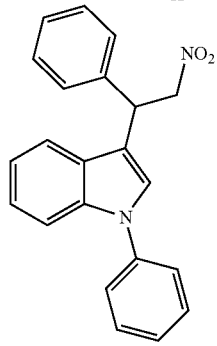
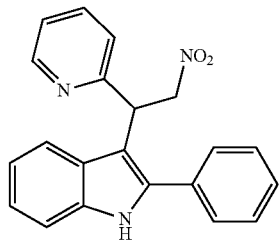
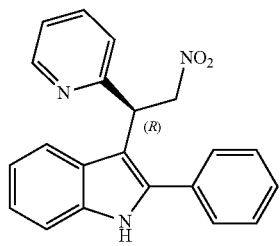
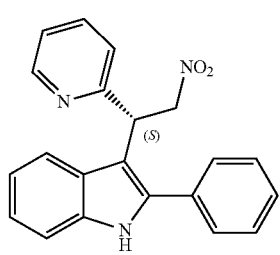
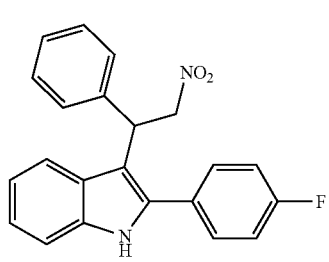
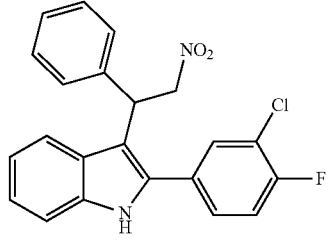
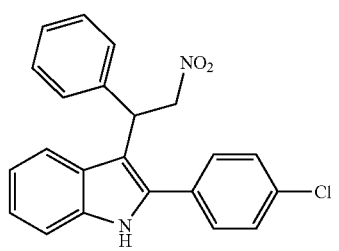

-continued

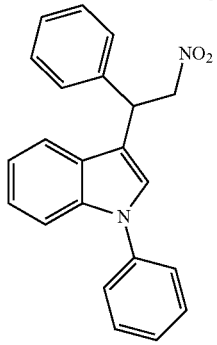

In yet another aspect, the present invention provides a method for treating a disorder in a mammalian species in need thereof, the method comprising administering to the mammalian species a therapeutically effective amount of at least one compound as described herein, wherein the disorder is selected from neurological and psychiatric disorders associated with endocannabinoid dysfunction and diseases in which the CB1 subtype of cannabinoid receptor is involved. These diseases include, but are not limited to, pain, central pain, peripheral pain, neuropathic pain, neuropathy, inflammatory pain, neurodegenerative diseases including multiple sclerosis, mental disorders such as schizophrenia and depression, mood disorders, memory disorders, addiction disorders, eating disorders (anorexia nervosa, bulimia nervosa, binge eating disorders), gastric motility disorders such as irritable bowel syndrome and diarrhea, anorexia related to chemotherapy and HIV, nausea associated with cancer chemotherapy, glaucoma.

In certain embodiments, the present invention provides a method for treating an eating disorder in a mammalian species in need thereof, the method comprising administering to the mammalian species a therapeutically effective amount of at least one compound as described herein, wherein the eating disorder is selected from anorexia nervosa, bulimia nervosa, and binge eating disorders.

In certain embodiments, the present invention provides a method for treating a neurodegenerative disorder in a mammalian species in need thereof, the method comprising administering to the mammalian species a therapeutically effective amount of at least one compound as described herein, wherein the neurodegenerative disorder is selected from Parkinson's disease, Huntington's disease, dementia, Alzheimer's disease, multi-infarct dementia, AIDS-related dementia, Fronto temperal Dementia, neurodegeneration associated with cerebral trauma, neurodegeneration associated with stroke, neurodegeneration associated with cerebral infarct, hypoglycemia-induced neurodegeneration, neurodegeneration associated with epileptic seizure, neurodegeneration associated with neurotoxin poisoning, and multi-system atrophy.

Utility and Methods of Use

Provided herein are methods for treating a disorder or disease by providing positive allosteric modulators of CB1 receptors. The methods, in general, comprise the step of administering a therapeutically effective amount of at least one compound of the present invention, or a pharmaceutically acceptable salt thereof, to a patient in need thereof to treat the disorder or disease.

In certain embodiments, this invention provides a use of at least one compound as described herein in the manufacture of a medicament for treating a disorder or disease associated with the CB1 cannabinoid receptor.

In certain embodiments, indications that may be treated with CB1 cannabinoid PAMs, either alone or in combination with other drugs, include, but are not limited to, those diseases in which the CB1 cannabinoid receptor is involved.

In certain embodiments, these indications include psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

The compounds of the invention are also useful for treatment of neurological and psychiatric disorders associated with endocannabinoid dysfunction and diseases in which the CB1 subtype of cannabinoid receptor is involved. These diseases include pain, central pain, peripheral pain, neuropathic pain, neuropathy, inflammatory pain, neurodegenerative diseases including multiple sclerosis, mental disorders such as schizophrenia and depression, mood disorders, memory disorders, addiction disorders, eating disorders (anorexia nervosa, bulimia nervosa, binge eating disorders), gastric motility disorders such as irritable bowel syndrome and diarrhea, anorexia related to chemotherapy and HIV, nausea associated with cancer chemotherapy, and glaucoma.

In certain embodiments, pain includes acute and chronic states, severe pain, intractable pain, neuropathic pain and post-traumatic pain.

In certain embodiments, the invention also relates to the use of a compound according to the invention, for the manufacture of a medicament for the treatment or prevention of any one of the disease conditions mentioned hereinbefore.

In view of the utility of the compounds according to the invention, there is provided a method of treating warm-blooded animals, including humans, suffering from any one of the diseases mentioned hereinbefore, and a method of preventing in warm-blooded animals, including humans, any one of the diseases mentioned hereinbefore.

Said methods comprise the administration, i.e., the systemic or topical administration, preferably oral administration, of a therapeutically effective amount of a compound according to the invention to warm-blooded animals, including humans.

Therefore, the invention also relates to a method for the prevention and/or treatment of any one of the diseases mentioned hereinbefore comprising administering a therapeutically effective amount of compound according to the invention to a patient in need thereof.

The CB1 allosteric modulators described herein can be used alone, in combination or in combination with other pharmaceutical agents such as other agents used in the treatment of the conditions described herein. In such combinations, the compounds of the present invention may be utilized in combination with one or more other drugs in the treatment, prevention, control, amelioration, or reduction of risk of diseases or conditions for which the compounds disclosed herein may have utility, where the combination of the drugs together are safer or more effective than either drug alone.

One skilled in the art will recognize that a therapeutically effective amount of the CB1 allosteric modulators of the present invention is the amount sufficient to potentiate the action of endocannabinoids and that this amount varies inter alia, depending on the type of disease, the concentration of the compound in the therapeutic formulation, and the condition of the patient. Generally, an amount of CB1 PAMs to be administered as a therapeutic agent for treating diseases, such as the disorders described herein, will be determined on a case-by-case basis by an attending physician.

Generally, a suitable dose is one that results in a concentration of the CB1 allosteric modulators at the treatment site in the range of 1 pM to 10 µM. The amount of a compound according to the present invention, also referred to here as the active ingredient, which is required to achieve a therapeutic effect may vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

Methods of Preparation:

Following are general synthetic schemes for manufacturing compounds of the present invention. These schemes are illustrative and are not meant to limit the possible techniques one skilled in the art any use to manufacture compounds disclosed herein. Different methods will be evident to those skilled in the art. Additionally, the various steps in the synthesis may be performed in an alternate sequence or order to give the desired compound(s). All documents cited herein are incorporated herein by reference in their entirety. For example, the following reactions are illustrations but not limitations of the preparation of some of the starting materials and examples used herein.

Nitrostyrenes required for building compounds of invention were synthesized by following literature reported procedures. Required aldehydes were purchased from commercial sources.

Nitrostyrene:

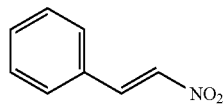

Reference: C. S. Marvel and W. H. Lycan *Org. Synth.* 1929, 9, 66 and *Org. Synth.* 1941, *Coll. Vol.* 1, 413.

(E)-2-(2-Nitrovinyl)furan

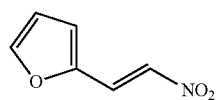

(E)-2-(2-nitrovinyl)furan

Reference: Org. Lett., 2006, 8 (11), pp 2373-2376.

(E)-(3-Nitroallyl)benzene

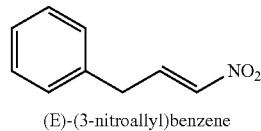 [SMILES: O=[N+]([O-])/C=C/Cc1ccccc1]

(E)-(3-nitroallyl)benzene

Reference: Kochany, J.; Piotrowska, H. Bulletin de l'Academie Polonaise des Sciences, Serie des Sciences Chimiques, 1976, vol. 24, p. 929-933.

(E)-4-(2-Nitro-vinyl)-biphenyl

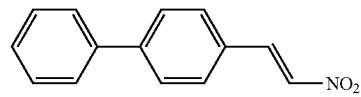

(E)-4-(2-nitrovinyl)-1,1'-biphenyl

Reference: Bioorganic & Medicinal Chemistry Volume 4, Issue 8, August 1996, Pages 1287-1297.

(E)-2-(2-nitrovinyl) pyridine

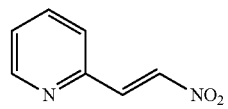 [SMILES: O=[N+]([O-])/C=C/c1ccccn1]

Reagents and conditions: a) 1,1,3,3-tetramethylguanidine, toluene, 50° C., 1 h; b) methanesulfonyl chloride, toluene, 0° C.

To a solution of picolinaldehyde (10 g, 93 mmol), nitromethane (17.10 g, 280 mmol) in 120 mL anhydrous toluene was added 1,1,3,3-tetramethylguanidine (22.58 g, 196 mmol) and reaction was stirred at 50° C. under inert conditions for 1 hr to give nitroalcohol. Reaction mixture was cooled to 0° C. followed by dropwise addition of methanesulfonyl chloride (23.53 g, 205 mmol) under inert conditions, and reaction was stirred at room temperature for 3 hrs Reaction was quenched by addition of 200 mL saturated NaHCO$_3$ solution, organic layer was separated, water layer was extracted 3 times with ethyl acetate, combined organic layers were washed with brine, dried over sodium sulfate, filtered, volatiles were removed under vacuum to give crude product, which was purified by flash chromatography using LUKNOVA column (4:1 Hex/EtOAc; 120 g column) to give pure (E)-2-(2-nitrovinyl) pyridine (5.12 g, 34.1 mmol, 36.5% yield). M.P. 84-87° C.

$^1$H NMR (500 MHz, CDCl$_3$) δ: 8.68 (dd, J=5.0 Hz, J=1.0 Hz, 1H), 8.02 (d, J=13.0 Hz, 1H), 7.92 (d, J=13.0 Hz, 1H), 7.79 (td, J=8.0 Hz, J=2.0 Hz, 1H), 7.48 (d, J=8.0 Hz, 1H), 7.38 (ddd, J=7.0 Hz, J=3.5 Hz, J=1.0 Hz, 1H).

Reference: Justin M. Lopchuk, Gordon W. Gribble *Tetrahedron Letters*, Volume 52, Issue 32, 2011, Pages 4106-4108

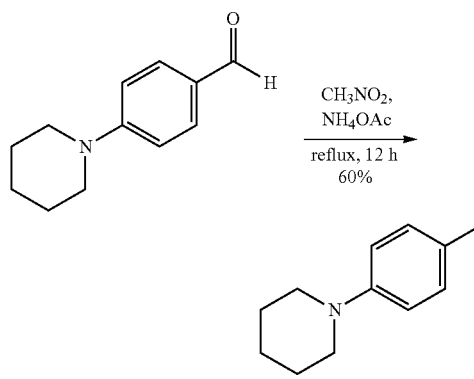

(E)-1-[4-(2-Nitrovinyl)phenyl]piperidine

To a stirred solution of 4-(Piperidin-1-yl)benzaldehyde (4 g, 211 mmol.) in 20 mL anhydrous nitromethane was added ammonium acetate (8 g, 140 mmol.) and the resulting mixture was refluxed under an argon atmosphere for 2 h. Solvent was removed under reduced pressure and reaction mixture was diluted with ethyl acetate and water. Organic layer was separated and aqueous layer extracted with EtOAc (6×30 mL). Combined organic layer was washed with water, brine and dried (MgSO$_4$). Evaporation of volatiles under reduced pressure gave crude which was purified by flash column chromatography (5%→20% EtOAc: Hexane) to give desired product as a dark orange crystalline solid (2.9 g, 60% yield). M.p.=110-112° C.; Rf=0.48 (EtOAc/Hexane=20/80). $^1$H NMR (500 Mz, CDCl$_3$): δ 7.95 (d, J=13.5 Hz, 1H), 7.50 (d, J=13.5 Hz, 1H), 7.42 (d, J=9.0 Hz, 2H), 6.86 (d, J=9.0 Hz, 2H), 3.40-3.36 (m, 4H), 1.67 (m as br s, 6H). Mass spectrum m/z—233.12 [M+H]$^+$ Some compounds (Compounds 2-7, 10-15) of present invention were synthesized by following general procedure depicted in Scheme-1.

Scheme 1:

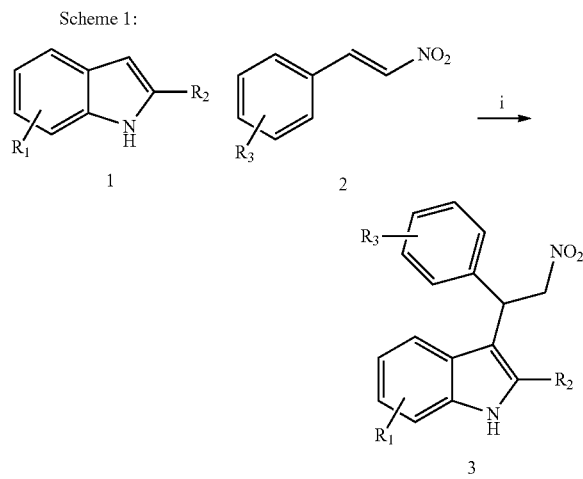

In a round bottom flask of suitable capacity 1H-indoles 1 (1 eq), nitrovinyl derivatives 2 (1.01 eq), tetraethylammonium bromide (1.1 eq) were taken in suitable amount of dioxan: water (3:1) and reaction was heated at 105° C. for 2-24 h. Solvents were removed under reduced pressure and residue was partitioned in DCM: Water. Combined DCM layer was washed with brine, dried (Na$_2$SO$_4$), organic solvents were removed under vacuum to give crude product which was purified by flash chromatography.

3-(2-Nitro-1-phenylethyl)-2-phenyl-1H-indole (Compound 1)

Yield=56%; $^1$H NMR (500 MHz, CDCl$_3$) δ: 8.15 (br s, 1H, NH), 7.53 (d, J=8.0 Hz, 1H), 7.48-7.40 (m, 5H), 7.38 (d, J=7.5 Hz, 1H), 7.33 (d, J=7.5 Hz, 2H), 7.29 (t, J=7.5 Hz, 2H), 7.26-7.19 (m, 2H), 7.11 (td, J=7. 5, 1.0 Hz, 1H), 5.32 (br t, J=7.5 Hz, 1H), 5.18 (dd, J=12.0, 7.5 Hz 1H,), 5.12 (dd, J=12.0 Hz, 8.5 Hz, 1H). Mass spectrum m/z—343.1 [M+H]$^+$. A portion of Compound 1 was purified to yield pair of enantiomers using supercritical fluid chromatography on chiralpak-IC column with isocratic MeOH: CO$_2$ (20:80) to give the faster eluting compound (compound 2) and slower eluting compound (compound 3). These compounds were recrystallized from methanol and their absolute stereochemistry was determined using X-ray crystallography.

R)-3-(2-Nitro-1-phenylethyl)-2-phenyl-1H-indole (Compound 2

$^1$H NMR (500 MHz, CDCl$_3$): δ 8.15 (br s, 1H, NH), 7.52 (d, J=8.5 Hz, 1H), 7.49-7.41 (m, 5H), 7.40 (d, J=8.0 Hz, 1H), 7.34 (d, J=7.5 Hz, 2H), 7.30 (t, J=7.5 Hz, 2H), 7.27-7.19 (m, 2H), 7.12 (td, J=7.5 Hz, 1.0 Hz, 1H), 5.32 (dd as br t, J=8.0 Hz, 1H), 5.19 (dd, J=12.0, 7.5 Hz, 1H), 5.12 (dd, J=12.0 Hz, J=8.0 Hz, 1H); Mass spectrum m/z—343.2 [M+H]$^+$. [α$_D$]=+88.36 (c=1 in MeOH).

S)-3-(2-Nitro-1-phenylethyl)-2-phenyl-1H-indole (Compound 3

$^1$H NMR (500 MHz, CDCl$_3$): δ 8.16 (br s, 1H, NH), 7.53 (d, J=8.5 Hz, 1H), 7.49-7.42 (m, 5H), 7.40 (d, J=8.0 Hz, 1H), 7.34 (d, J=7.5 Hz, 2H), 7.30 (t, J=7.5 Hz, 2H), 7.26-7.19 (m, 2H), 7.12 (td, J=7.5 Hz, 1.0 Hz, 1H), 5.33 (dd as br t, J=8.0 Hz, 1H), 5.19 (dd, J=12.0, 7.5 Hz, 1H), 5.13 (dd, J=12.0 Hz, J=8.0 Hz, 1H); Mass spectrum m/z—343.2 [M+H]$^+$. [α$_D$]=−88.68 (c=1 in MeOH).

3-(2-Nitro-1-(4-(piperidin-1-yl)phenyl)ethyl)-2-phenyl-1H-indole (Compound 4)

Yield=57.4%, $^1$H NMR (500 MHz, CDCl$_3$) δ 8.14 (br s, 1H, NH), 7.54 (d, J=7.5 Hz, 1H), 7.46-7.39 (m, 5H), 7.38 (d, J=8.0 Hz, 1H), 7.23-7.18 (m, 3H, especially 7.20, d, J=8.0 Hz), 7.11 (t, J=7.5 Hz, 1H), 6.84 (d, J=9.0 Hz, 2H), 5.23 (dd as br t, J=8.0 Hz, 1 Hz), 5.15-5.07 (m, 2H), 3.11 (br t, J=5.5 Hz, 4H), 1.71-1.64 (m, 4H), 1.58-1.52 (m, 2H). Mass spectrum m/z—426.3 [M+H]$^+$.

3-(1-([1,1'-Biphenyl]-4-yl)-2-nitroethyl)-2-phenyl-1H-indole (Compound 5)

Yield=91.6%; $^1$H NMR (500 MHz, CDCl$_3$): δ 8.18 (br s, 1H, NH), 7.59-7.51 (m, 5H), 7.50-7.39 (m, 10H), 7.33 (tt, J=7.5 Hz, J=1.5 Hz, 1H), 7.24 (t, J=8.0 Hz, 1H), 7.14 (t, J=8.0 Hz, 1H), 5.37 (br t, J=8.0 Hz, 1H), 5.23 (dd, J=12.0 Hz, J=7.5 Hz, 1H), 5.17 (dd, J=13.0 Hz, J=8.0 Hz, 1H). Mass spectrum m/z—419.2 [M+H]$^+$.

2-(2-(Naphthalen-2-yl)-1H-indol-3-yl)-2-phenylethanamine (Compound 6)

Yield=87.4%; $^1$H NMR (500 MHz, CDCl$_3$): δ 8.28 (br s, 1H, NH), 7.94 (d, J=8.5 Hz, 1H), 7.92-7.88 (m, 2H, especially 7.91, s, 1H), 7.87-7.82 (m, 1H), 7.61-7.53 (m, 4H), 7.44 (d, J=8.0 Hz, 1H), 7.38 (d, J=7.5 Hz, 2H), 7.33 (t, J=7.5 Hz, 2H), 7.28-7.20 (m, 2H), 7.15 (t, J=7.5 Hz, 1H), 5.42 (br t, J=8.5 Hz, 1H), 5.24-5.15 (m, 2H). Mass spectrum m/z—393.2 [M+H]$^+$.

5-Chloro-3-(2-nitro-1-phenylethyl)-2-phenyl-1H-indole (Compound 7)

Yield=51.5%; $^1$H NMR (500 MHz, CDCl$_3$): δ 8.18 (br s, 1H, NH), 7.50-7.42 (m, 6H, especially 7.45, br s, 1H), 7.35-7.25 (m, 6H), 7.17 (dd, J=8.5 Hz, 1.5 Hz, 1H), 5.28 (dd, J=9.0 Hz, 7.0 Hz, 1H), 5.15 (dd, J=12.5 Hz, 7.0 Hz, 1H), 5.10 (dd, J=13.0 Hz, 8.5 Hz, 1H). Mass spectrum m/z—377.2 [M+H]$^+$.

3-(3-Nitrophenyl)-2-phenyl-1H-indole (Compound 8)

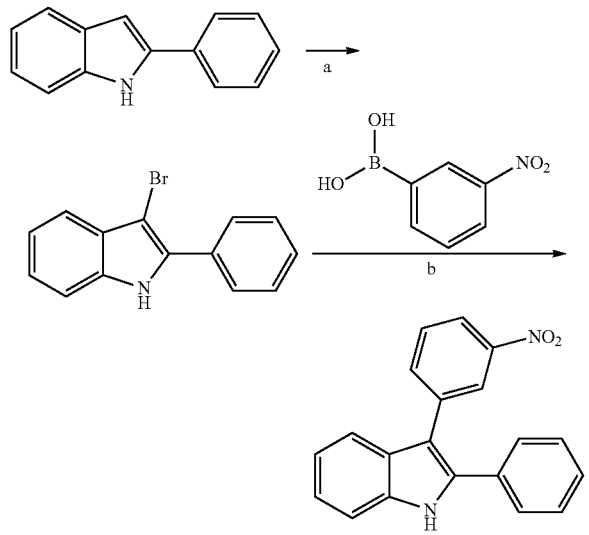

Reagents and conditions: c) NBS, DMF, argon, 0° C.; d) DME, Tetrakis(triphenylphosphine)palladium(0), Ba(OH)$_2$, 150° C., MW, 1 h.

3-Bromo-2-phenyl-1H-indole

In a 100 ml round bottom flask 2-phenyl-1H-indole (1 g, 5.17 mmol) was taken in 5 mL of anhydrous DMF followed by drop wise addition of solution of 1-bromopyrrolidine-2,5-dione (0.967 g, 5.43 mmol) in 5 ml anhydrous DMF and reaction was stirred at 25° C. under inert conditions for 3 h. Reaction mixture was poured on 500 g of crushed ice and stirred vigorously. Solid was filtered, air dried to give crude product, which was recrystallized from ethanol to give pure 3-bromo-2-phenyl-1H-indole (1.25 g, 4.59 mmol, 89% yield) M.P.: 108° C.

$^1$H NMR (500 MHz, CDCl$_3$) δ: 8.57 (br s, 1H, NH), 7.78 (d, J=7.5 Hz, 2H), 7.59 (d, J=8.0 Hz, 1H), 7.45 (t, J=7.5 Hz, 2H), 7.37 (d, J=7.5 Hz, 1H), 7.32 (d, J=8.0 Hz, 1H), 7.20 (tt, J=15.5 Hz, J=7.5 Hz, 2H).

References: (a) Paola Barraja, Patrizia Diana, Anna Carbone, Girolamo Cirrincione Tetrahedron 64 (2008) 11625-11631. (b) Duckhyun Kim, Moon-Sung Kang, Kihyung Song, Sang Ook Kang, Jaejung Ko Tetrahedron 64 (2008) 10417-10424.

3-(3-Nitrophenyl)-2-phenyl-1H-indole

In a 20 mL microwave vial 3-bromo-2-phenyl-1H-indole (500 mg, 1.837 mmol), (3-nitrophenyl)boronic acid (337 mg, 2.021 mmol), tetrakis(triphenylphosphine)palladium(0) (212 mg, 0.184 mmol), barium hydroxide (944 mg, 5.51 mmol) were taken in DME (12 mL). The vial was sealed and reaction was heated at 150° C. under microwave conditions for 60 min, cooled to room temp, solvents were removed under high vacuum and residue was diluted with water, partitioned in DCM: water and separated. Organic layer was washed with brine, dried over sodium sulfate, filtered and conc under vacuum to give crude product which was purified by flash chromatography using LUKNOVA column (4:1 Hex/EtOAc; 40 g column) to give pure 3-(3-nitrophenyl)-2-phenyl-1H-indole (360 mg, 1.145 mmol, 62.3% yield). $^1$H NMR (500 MHz, CDCl$_3$) δ 8.35 (m as br s, 2H), 8.13 (ddd, J=8.5 Hz, J=2.5 Hz, J=1.0 Hz, 1H), 7.71 (dt, J=7.5 Hz, 1.5 Hz, 1H), 7.68 (d, J=8.5 Hz, 1H), 7.51 (d, J=8.0 Hz, 1H), 7.48 (d, J=8.0 Hz, 1H), 7.42-7.34 (m, 5H), 7.30 (td, J=8.0 Hz, 1.5 Hz, 1H), 7.22 (td, J=8.0 Hz, 1.5 Hz, 1H). Mass spectrum m/z—315.2 [M+H]$^+$.

3-(2-Nitro-1-phenylethyl)-1-phenyl-1H-indole (Compound 9)

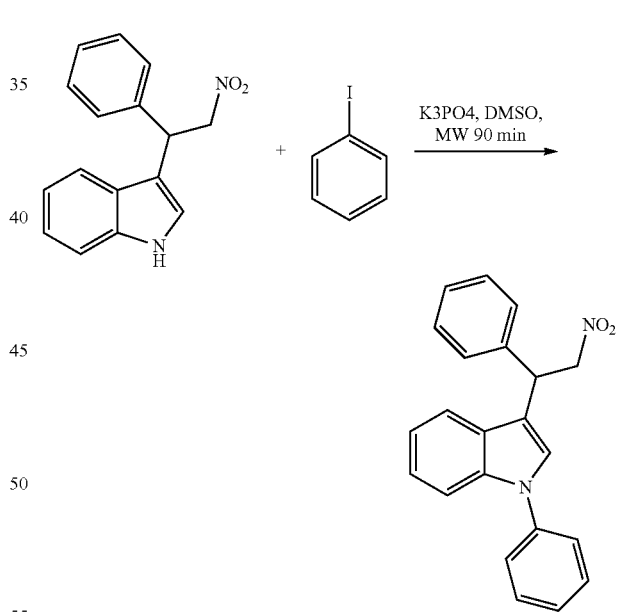

In a microwave vial 3-(2-nitro-1-phenylethyl)-1H-indole (200 mg, 0.751 mmol), iodobenzene (306 mg, 1.502 mmol), K$_3$PO$_4$ (478 mg, 2.253 mmol) in DMSO were taken, the vial was sealed and heated to 150° C. in microwave for 90 min. Reaction mixture was cooled to room temperature, diluted with water and extracted with dichloromethane. The organic layer was separated and washed with brine and dried (Na$_2$SO$_4$). Evaporation of volatiles under reduced pressure followed by purification of crude by column chromatography (5:1 Hex/EtOAc; 40 g column) gave 65 mg of desired product. Yield=25.3%; $^1$H NMR (500 MHz, CDCl$_3$): δ

7.54-7.45 (m, 6H), 7.42-7.32 (m, 5H), 7.27 (tt, J=7.5 Hz, J=1.5 Hz, 1H), 7.22 (td, J=8.0 Hz, J=1.0 Hz, 1H), 7.17 (s, 1H), 7.13 (td, J=7.5 Hz, 1.5 Hz, 1H), 5.25 (dd as br t, J=7.5 Hz, 1H), 5.11 (dd, J=12.5 Hz, J=7.5 Hz, 1H), 4.98 (dd, J=12.5 Hz, J=8.5 Hz, 1H). Mass spectrum m/z—343.2 [M+H]$^+$.

3-(2-Nitro-1-(pyridin-2-yl)ethyl)-2-phenyl-1H-indole (Compound 10)

Yield=83%; $^1$H NMR (500 MHz, CDCl$_3$): δ 8.54 (dd, J=5.0 Hz, 1.0 Hz, 1H), 8.20 (s, 1H, NH), 7.56-7.41 (m, 6H), 7.38 (d, J=7.5 Hz, 1H), 7.34 (d, J=7.5 Hz, 1H), 7.18 (td, J=7.5 Hz, J=1.5 Hz, 1H), 7.11 (dd, J=8.0 Hz, J=5.0 Hz, 1H), 7.08 (d, J=7.5 Hz, 1H), 7.02 (td, J=7.5 Hz, J=1.0 Hz, 1H), 5.81 (dd, J=13.5 Hz, J=8.0 Hz, 1H), 5.48 (t, J=7.5 Hz, 1H), 4.95 (dd, J=14.0 Hz, J=7.5 Hz, 1H). Mass spectrum m/z—344.2 [M+H]$^+$.

A portion of Compound 10 was purified to yield pair of enantiomers using supercritical fluid chromatography on chiralpak-IC column with isocratic IPA: CO$_2$ (20:80) to give the faster eluting compound (compound 11) and slower eluting compound (compound 12). These compounds were recrystallized from methanol and their absolute stereochemistry was determined using X-ray crystallography.

R)-3-(2-nitro-1-(pyridin-2-yl)ethyl)-2-phenyl-1H-indole (Compound 11

$^1$H NMR (500 MHz, CDCl$_3$): δ 8.55 (dd, J=5.0 Hz, 1.0 Hz, 1H), 8.17 (s, 1H, NH), 7.57-7.41 (m, 6H), 7.39 (d, J=7.5 Hz, 1H), 7.34 (d, J=8.0 Hz, 1H), 7.18 (td, J=7.5 Hz, J=1.5 Hz, 1H), 7.11 (dd, J=8.0 Hz, J=5.0 Hz, 1H), 7.08 (d, J=7.5 Hz, 1H), 7.02 (td, J=7.5 Hz, J=1.0 Hz, 1H), 5.81 (dd, J=14.0 Hz, J=8.5 Hz, 1H), 5.48 (t, J=7.5 Hz, 1H), 4.95 (dd, J=14.0 Hz, J=7.5 Hz, 1H). Mass spectrum m/z—344.2 [M+H]$^+$. [α$_D$]=+353 (c=1 in MeOH).

S)-3-(2-nitro-1-(pyridin-2-yl)ethyl)-2-phenyl-1H-indole (Compound 12

$^1$H NMR (500 MHz, CDCl$_3$): δ 8.56 (dd, J=4.5 Hz, 1.0 Hz, 1H), 8.17 (s, 1H, NH), 7.57-7.41 (m, 6H), 7.39 (d, J=7.5 Hz, 1H), 7.35 (d, J=8.0 Hz, 1H), 7.17 (td, J=7.5 Hz, J=1.5 Hz, 1H), 7.11 (dd, J=8.0 Hz, J=5.0 Hz, 1H), 7.08 (d, J=7.5 Hz, 1H), 7.02 (td, J=7.5 Hz, J=1.0 Hz, 1H), 5.81 (dd, J=14.0 Hz, J=8.5 Hz, 1H), 5.47 (t, J=7.5 Hz, 1H), 4.95 (dd, J=14.0 Hz, J=7.5 Hz, 1H). Mass spectrum m/z—344.2 [M+H]$^+$. [α$_D$]=−352.7 (c=1 in MeOH).

2-(4-Fluorophenyl)-3-(2-nitro-1-phenylethyl)-1H-indole (Compound 13)

Yield=68%; $^1$H NMR (500 MHz, DMSO d$_6$): δ 11.47 (s, 1H, NH), 7.64 (d, J=8.0 Hz, 1H), 7.59-7.55 (m, 2H, especially, 7.56, dd, J=9.0 Hz, J=5.5 Hz, 1H), 7.43-7.36 (m, 3H, especially, 7.41, d, J=8.5 Hz, 1H and 7.38, d, J=8.0 Hz, 1H), 7.34-7.26 (m, 4H), 7.21 (tt, J=7.0 Hz, J=1.5 Hz, 1H), 7.11 (td, J=7.0 Hz, J=1.0 Hz, 1H), 6.98 (td, J=7.5 Hz, J=1.0 Hz, 1H), 5.55 (dd, J=13.0 Hz, J=8.0 Hz, 1H), 5.44 (dd, J=13.0 Hz, J=8.5 Hz, 1H), 5.15 (dd as br t, J=8.0 Hz, 1H). Mass spectrum m/z—361.2 [M+H]$^+$.

2-(4-Chlorophenyl)-3-(2-nitro-1-phenylethyl)-1H-indole (Compound 14)

Yield=71.3%; $^1$H NMR (500 MHz, DMSO-d$_6$): δ 11.51 (s, 1H, NH), 7.66-7.60 (m, 3H, especially 7.63, d, J=8.5 Hz, 2H), 7.5 (d, J=8.0 Hz, 2H), 7.38 (d, J=8.0 Hz, 1H), 7.34-7.26 (m, 4H), 7.22 (tt, J=7.0 Hz, J=1.5 Hz, 1H), 7.12 (t, J=7.0 Hz, 1H), 6.98 (t, J=7.0 Hz, 1H), 5.55 (dd, J=13.5 Hz, J=7.5 Hz, 1H), 5.44 (dd, J=13.0 Hz, J=8.5 Hz, 1H), 5.17 (dd as br t, J=8.5 Hz, 1H). Mass spectrum m/z—377.2 [M+H]$^+$.

2-(3-Chloro-4-fluorophenyl)-3-(2-nitro-1-phenylethyl)-1H-indole (Compound 15)

Yield=72%; $^1$H NMR (500 MHz, DMSO-d$_6$): δ 11.56 (s, 1H, NH), 7.71 (dd, J=7.5 Hz, J=2.5 Hz, 1H), 7.66 (d, J=8.5 Hz, 1H), 7.63 (t, J=8.5 Hz, 1H), 7.53 (ddd, J=8.5 Hz, J=4.5 Hz, J=2.5 Hz, 1H), 7.38 (d, J=8.0 Hz, 1H), 7.34-7.27 (m, 4H), 7.22 (tt, J=7.0 Hz, J=1.5 Hz, 1H), 7.13 (td, J=7.5 Hz, 1.5 Hz, 1H), 6.99 (td, J=7.0 Hz, 1.0 Hz, 1H), 5.58 (dd, J=13.0 Hz, J=8.5 Hz, 1H), 5.47 (dd, J=13.0 Hz, J=8.5 Hz, 1H), 5.15 (dd as br t, J=8.5 Hz, 1H). Mass spectrum m/z—395.2 [M+H]$^+$.

Pharmaceutical Compositions

This invention also provides a pharmaceutical composition comprising at least one of the compounds as described herein or a pharmaceutically-acceptable salt thereof, and a pharmaceutically-acceptable carrier.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present pharmaceutical agents may be provided in the form of pharmaceutically-acceptable salts. The term "pharmaceutically-acceptable salt," in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., (1977) "Pharmaceutical Salts," *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, butionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra.)

Wetting agents, emulsifiers and lubricants, such as sodium lauryl sulfate, magnesium stearate, and polyethylene oxide-polybutylene oxide copolymer as well as coloring agents, release agents, coating agents, sweetening, flavoring and perfuming agents, preservatives and antioxidants can also be present in the compositions.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient, which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polybutylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxybutylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxybutylmethyl cellulose in varying butortions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples are embedding compositions, which can be used include polymeric substances and waxes. The active ingredient can also be in micro-encapsulated form with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxybutyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention.

Formulations of the present invention which are suitable for vaginal administration also include pessaries, tampons, creams, gels, pastes, foams or spray formulations containing such carriers as are known in the art to be apbutriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or butellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary butellants, such as chlorofluorohydrocarbons and volatile unsubstituted hydrocarbons, such as butane and butane.

Transdermal patches have the added advantage of providing controlled delivery of a compound of the present invention to the body. Such dosage forms can be made by dissolving, or dispersing the pharmaceutical agents in the buter medium. Absorption enhancers can also be used to increase the flux of the pharmaceutical agents of the invention across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle. One strategy for depot injections includes the use of polyethylene oxide-polybutylene oxide copolymers wherein the vehicle is fluid at room temperature and solidifies at body temperature.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions, which are compatible with body tissue.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another agent for treating the same disorder), or they may achieve different effects (e.g., control of any adverse effects).

The compounds of the invention may be administered intravenously, intramuscularly, intraperitoneally, subcutaneously, topically, orally, or by other acceptable means. The compounds may be used to treat arthritic conditions in mammals (i.e., humans, livestock, and domestic animals), birds, lizards, and any other organism, which can tolerate the compounds.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance which can be adapted to the practice of this invention in its various embodiments and equivalents thereof.

Examples

Rectal Temperature (hypothermia): Rectal temperature is measured in male CD-1 mice (weight: 25 to 30 g) using a rectal probe of a digital laboratory thermometer, RET-3-ISO, type T thermocouple, (Physitemp Instruments Inc, Clifton, N.J.). The lubricated probe is inserted approximately 2 cm into the rectum for ~30 sec, prior to each recording. The number of post-injection (i.p.) measurements taken were based on the duration of effect for each individual test agent (n=8/dose). Hypothermia is a common endpoint in cannabinoid research. Changes in temperature results are provided in FIG. 1.

Tail-Flick (analgesia): CD-1 mice (n=8/dose) of the same weight as described above were assessed for their base-line reaction time in a tail immersion test, with the intensity set at 52.0±0.5° C. In this tail immersion procedure, each mouse (wrapped in a small padding bag) was handheld, with approximately 2 cm of the tip of the tail immersed into a water bath and the latency for the animal to withdraw its tail from the water within 10 sec was scored. The tail withdrawal data is depicted as percent maximum possible effect (MPE), in which % MPE=100*(post injection latency−pre injection latency)/(10-sec ceiling−pre-injection latency). The 10 sec cut-off time limit is to minimize tissue damage. As above, drugs were administered i.p. and the number of post-injection (i.p.) measurements taken were based on the duration of effect for each individual test compound. Analgesia is a major focus in current cannabinoid research.

Figure 2:
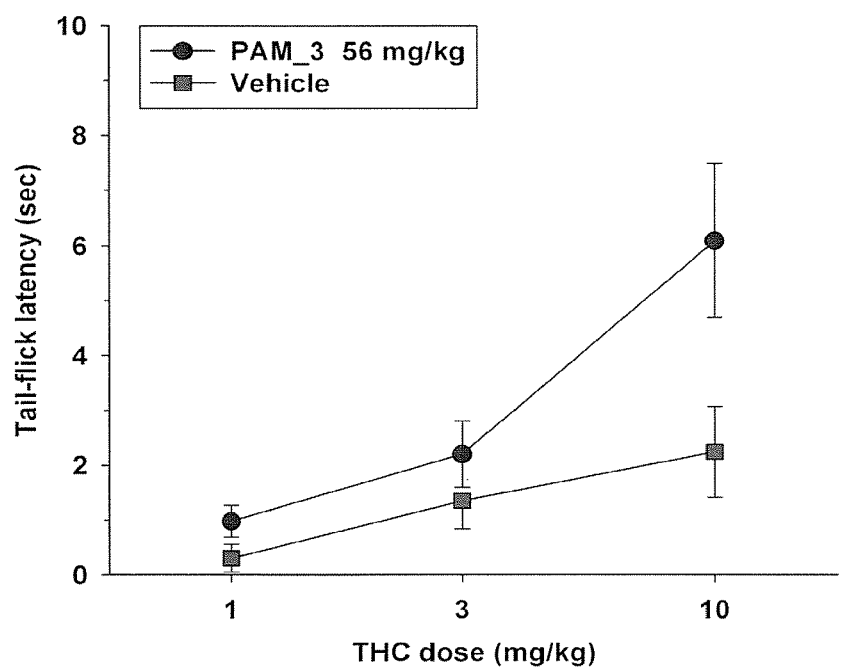
FIG. 2. is a graph of tail flick latency as a function of dose.

Data Analysis: Results are presented as the mean±SEM. Significant differences are calculated by means of analysis of variance (ANOVA) followed by Holm-Sidak multiple comparison post hoc statistical test procedure using the software SigmaStat (v.3.1; SysStat®). Differences are considered significant at the P<0.05 level. Results for PAM-3 ((3-(2-nitro-1-(4-(piperidin-1-yl)phenyl)ethyl)-2-phenyl-1H-indole) are provided in FIG. 2.

In Vivo Microdialysis Experiment:

Concentric microdialysis probes with 2 mm-long dialysis membranes were prepared as described previously (Pontieri, Tanda & DiChiara 1995). Sprague-Dawley male rats were anesthetized with Equithesin and probes were surgically implanted in the shell of nucleus accumbens (coordinates with respect to bregma: anterior, +2.2; lateral, −1.0; vertical −8.0 from dura). Ringer's solution (147 mM NaCl, 2.2 mM $CaCl_2$, 4.0 mM KCl) was pumped through the dialysis probe at a constant flow rate of 1uL/minute. Compound 1 (PAM1; 30 mg/kg) was dissolved in 4% DMSO, 8% PEG and 8% Tween (in sterile water) and it was injected IP after the third stable basal. Collection of dialysate samples started after 20 minutes, with samples collected every 20 minutes and immediately analyzed by a high-performance liquid chromatography system coupled to electrochemical detection to quantify dopamine.

Figure 3:
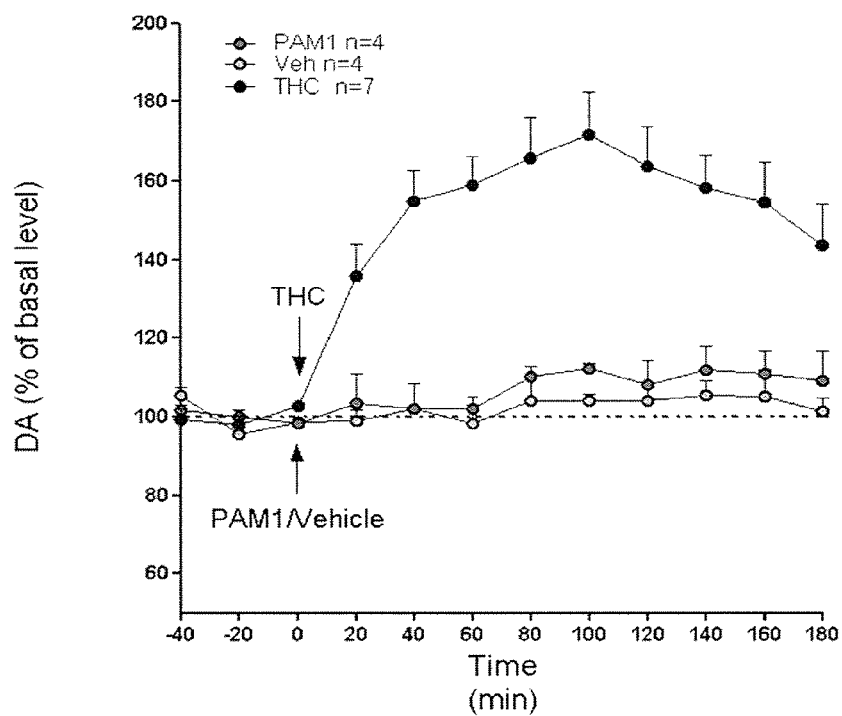
FIG. 3. is a graph of microdialysis experiment with Compound 1 to show its effect on dopamine level in nucleus accumbens.

Results are presented as group means (±SEM). Microdialysis data were analyzed using two-way ANOVA. As shown in FIG. 3, there was no significant change in extracellular dopamine levels after PAM1 injection (ANOVA, p=0.325, NS). Results for the experiment are shown in FIG. 3.

In Vitro Evaluation:

Cell Handling: cAMP Hunter cell lines were expanded from freezer stocks in T25 flasks according to standard procedures and maintained in selective growth media prior to assay. Once it was established that the cells were healthy and growing normally, cells were passaged from flasks using cell dissociation reagent buffer and seeded into white walled clear bottom 384-well microplates for compound profiling. For profiling, cells were seeded at a density of 10000 cells per well in a total volume of 20 μL and were allowed to adhere and recover overnight prior to compound addition. Cells were treated the following day using the protocols shown below. cAMP modulation was determined using the DiscoveRx HitHunter cAMP XS+ assay.

Media was aspirated from cells and replaced with 10 μL 1:1 HBSS/Hepes: cAMP XS+Ab reagent. Agonist (CP55,940) dose curves were performed to determine the $EC_{20}$ value for the following testing with compounds. 5 μL of 4× agonist was added to each well with an equal concentration of vehicle present. $EC_{20}$ agonist concentration was determined directly from agonist dose curve.

For allosteric determination, cells were preincubated with compound followed by agonist challenge at the EC20 concentration. 5 μL of 4× compound was added to cells and incubated at 37° C. for 30 minutes. 5 μL of 4×$EC_{20}$ agonist was added to cells and incubated at 37° C. for 30 minutes.

Signal Detection: After appropriate compound incubation, assay signal was generated through incubation with 20 μL cAMP XS+ ED/CL lysis cocktail for one hour followed by incubation with 20 μL cAMP XS+ EA reagent for three hours at room temperature. Microplates were read following signal generation with a PerkinElmer Envision™ instrument for chemiluminescent signal detection.

Data Analysis: Dose curves were plotted using GraphPad Prism or Activity Base. The percentage activity is calculated using the following formula:

% Activity=100%×(1−(mean RLU of test sample−mean RLU of MAX control)/(mean RLU of vehicle control [$EC_{20}$ for PAM]−mean RLU of MAXcontrol).

Agonist (CP55,940) dose curves were performed for the CNR1 PathHunter and cAMP Hunter cell lines. Data shown was normalized to the maximal and minimal response observed in the presence of control ligand and vehicle respectively. The cAMP assay was performed in the presence of 20 μM forskolin ($EC_{80}$).

TABLE 1

Functional data of representative compounds.

| Compound # | Structure | cAMP activity (nM) | Emax (%) |
|---|---|---|---|
| 1 (PAM1) (comparative) | 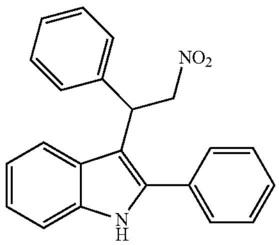 [SMILES: O=[N+]([O-])CC(c1ccccc1)c1c(-c2ccccc2)[nH]c2ccccc12] | 1342 | 80 |
| 2 | (R) | 1597 | 75 |
| 3 | (S) | 370 | 96 |
| 4 (PAM3) | 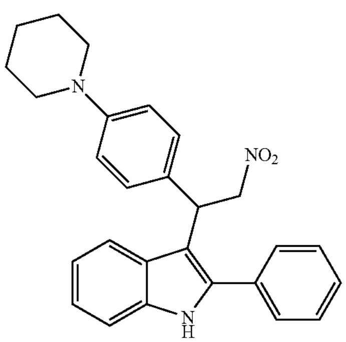 [SMILES: O=[N+]([O-])CC(c1ccc(N2CCCCC2)cc1)c1c(-c2ccccc2)[nH]c2ccccc12] | 590 | 101 |
| 5 | 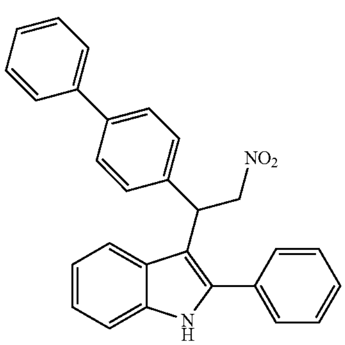 [SMILES: O=[N+]([O-])CC(c1ccc(-c2ccccc2)cc1)c1c(-c2ccccc2)[nH]c2ccccc12] | >10,000 | 0 |

TABLE 1-continued
Functional data of representative compounds.
| Compound # | Structure | cAMP activity (nM) | Emax (%) |
|---|---|---|---|
| 6 | 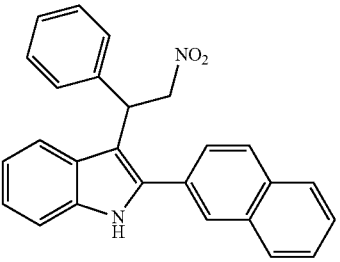 [SMILES: O=[N+]([O-])CC(c1ccccc1)c1c(-c2ccc3ccccc3c2)[nH]c2ccccc12] | 744 | 65 |
| 7 | 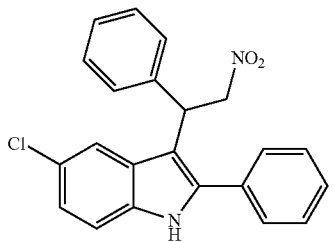 [SMILES: O=[N+]([O-])CC(c1ccccc1)c1c(-c2ccccc2)[nH]c2ccc(Cl)cc12] | 1006 | 44 |
| 8 | 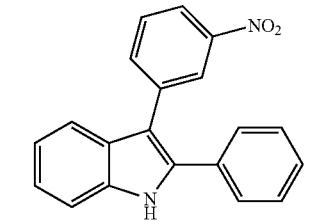 [SMILES: O=[N+]([O-])c1cccc(-c2c(-c3ccccc3)[nH]c3ccccc23)c1] | >10,000 | 54 |
| 9 | 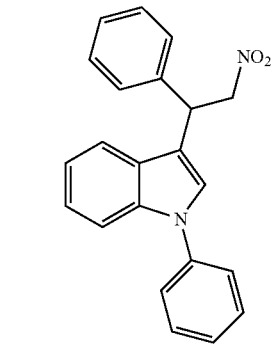 [SMILES: O=[N+]([O-])CC(c1ccccc1)c1cn(-c2ccccc2)c2ccccc12] | 920 | 105 |
| 10 | 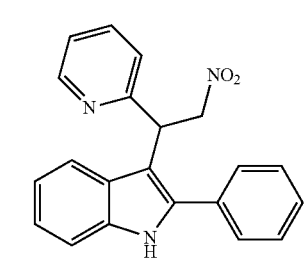 [SMILES: O=[N+]([O-])CC(c1ccccn1)c1c(-c2ccccc2)[nH]c2ccccc12] | 456 | 96 |

TABLE 1-continued

Functional data of representative compounds.

| Compound # | Structure | cAMP activity (nM) | Emax (%) |
|---|---|---|---|
| 11 | 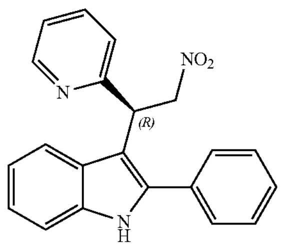 | 300 | 120 |
| 12 | 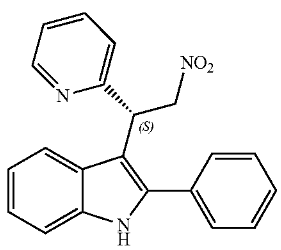 | 417 | 119 |
| 13 | 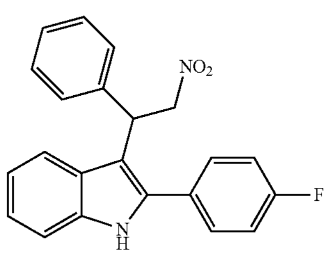 [SMILES: O=[N+]([O-])CC(c1ccccc1)c1c(-c2ccc(F)cc2)[nH]c2ccccc12] | 327 | 110 |
| 14 | 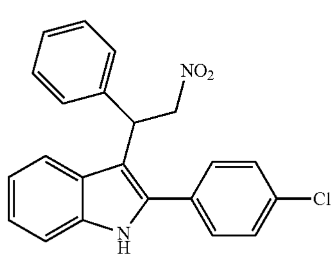 [SMILES: O=[N+]([O-])CC(c1ccccc1)c1c(-c2ccc(Cl)cc2)[nH]c2ccccc12] | 650 | 115 |

TABLE 1-continued

Functional data of representative compounds.

| Compound # | Structure | cAMP activity (nM) | Emax (%) |
|---|---|---|---|
| 15 | 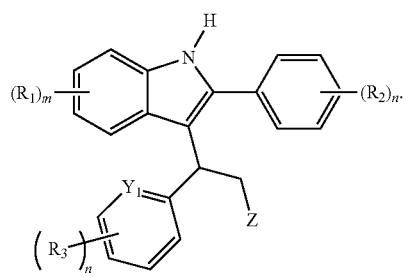 | 411 | 110 |

The invention claimed is:

1. A compound having the following structure, or a pharmaceutically acceptable salt thereof:

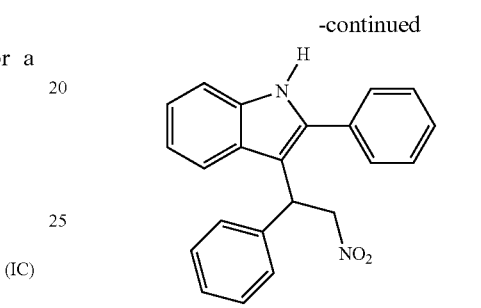

(IC)

wherein $Y_1$ is C or N;

Z is $NO_2$;

each $R_1$ is independently H, halogen, OH, CN, $(C_1\text{-}C_6)$ alkyl, or haloalkyl;

each $R_2$ is independently H, halogen, OH, or CN;

each $R_3$ is independently H, OH, CN, or piperdinyl;

m is 1-4; and n is 1-5; provided the compound is not:

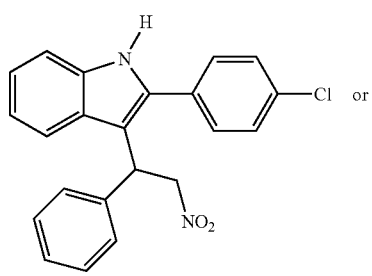

2-(4-chlorophenyl)-3-(2-nitro-1-phenylethyl)-1H-indole

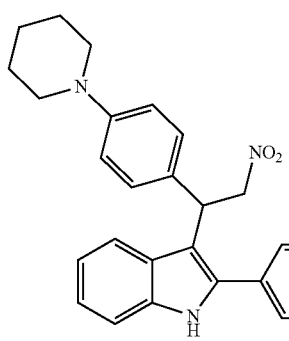

3-(2-nitro-1-phenylethyl)-2-phenyl-1H-indole.

2. The compound of claim 1, wherein the compound is a compound of structure (IC) and at least one $R_2$ is selected from the group consisting of Cl and F.

3. The compound of claim 1, wherein the compound is a compound of structure (IC) and $Y_1$ is C.

4. A compound having a structure selected from the group consisting of:

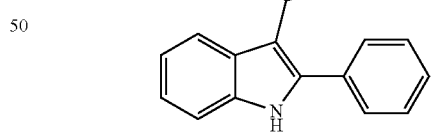

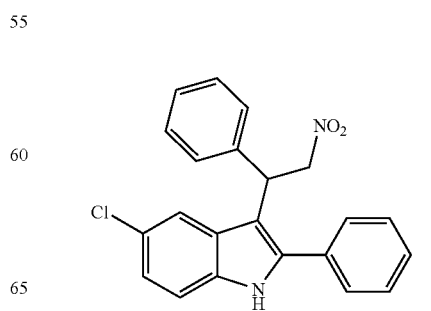

-continued

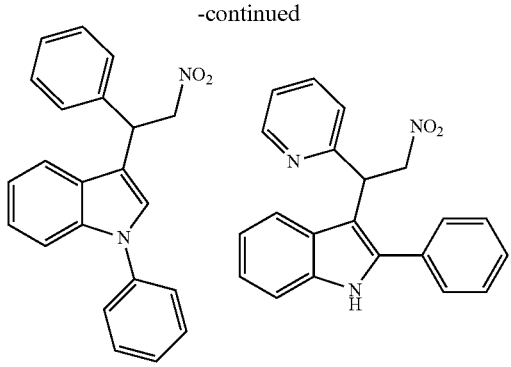

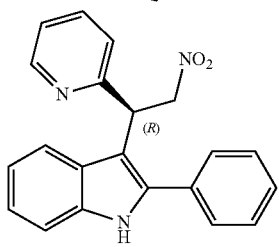

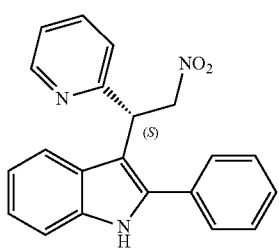

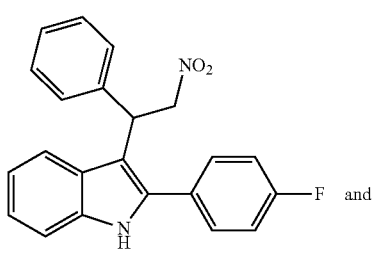

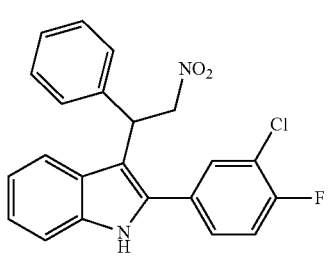 [SMILES: O=[N+]([O-])CC(c1ccccc1)c1c(-c2ccc(F)c(Cl)c2)[nH]c2ccccc12]

or a pharmaceutically acceptable salt thereof.

5. A pharmaceutical composition comprising a pharmaceutically-acceptable carrier or diluent and at least one compound having the following structure, or a pharmaceutically acceptable salt thereof:

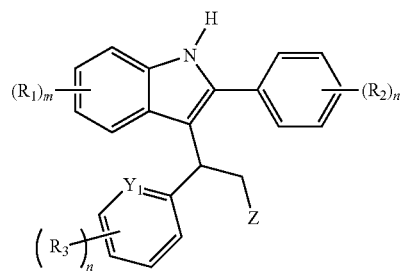

wherein $Y_1$ is C or N;
Z is $NO_2$;
each $R_1$ is independently H, halogen, OH, CN, ($C_1$-$C_6$) alkyl, or haloalkyl;
each $R_2$ is independently H, halogen, OH, or CN;
each $R_3$ is independently H, OH, CN, or piperdinyl;
m is 1-4; and
n is 1-5; provided the compound is not:

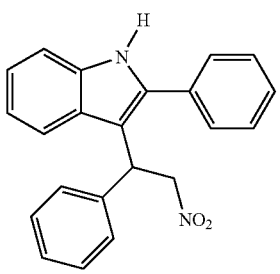

3-(2-nitro-1-phenylethyl)-2-phenyl-1H-indole.

6. The pharmaceutical composition of claim 5, wherein the compound is a compound of structure (IC) and at least one $R_2$ is selected from the group consisting of Cl and F.

7. A pharmaceutical composition comprising a pharmaceutically-acceptable carrier or diluent and at least one compound selected from the group consisting of:

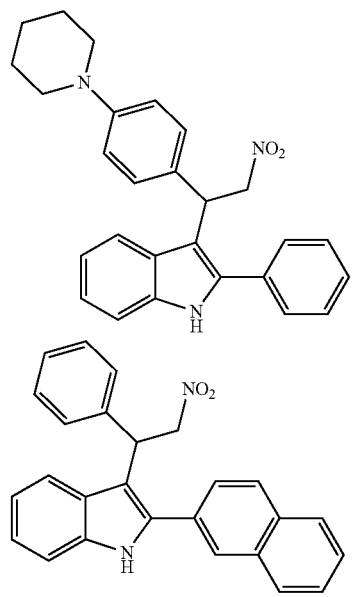

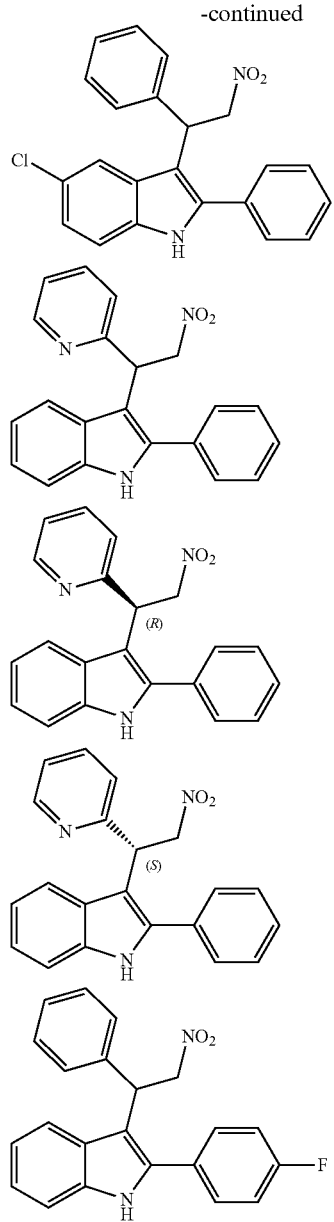
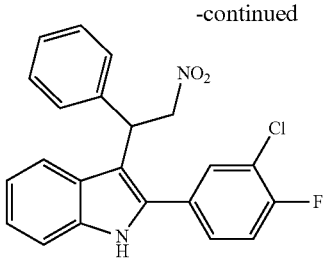
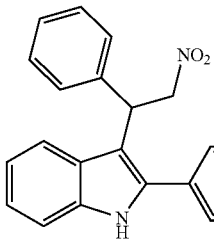
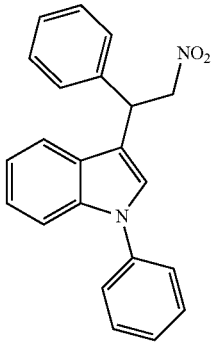
or a pharmaceutically acceptable salt thereof.
* * * * *